(12) United States Patent
Kasama et al.

(10) Patent No.: US 11,382,980 B2
(45) Date of Patent: Jul. 12, 2022

(54) OIL/FAT COMPOSITION CONTAINING POLYUNSATURATED FATTY ACID

(71) Applicants: Yuuki Kasama, Yokkaichi (JP); Etsuko Tominaga, Yokkaichi (JP)

(72) Inventors: Yuuki Kasama, Yokkaichi (JP); Etsuko Tominaga, Yokkaichi (JP)

(73) Assignee: TAIYO KAGAKU CO., LTD., Yokkaichi (JP)

( * ) Notice: Subject to any disclaimer, the term of this patent is extended or adjusted under 35 U.S.C. 154(b) by 0 days.

(21) Appl. No.: 15/027,919

(22) PCT Filed: Oct. 7, 2014

(86) PCT No.: PCT/JP2014/076767
§ 371 (c)(1),
(2) Date: Apr. 7, 2016

(87) PCT Pub. No.: WO2015/053252
PCT Pub. Date: Apr. 16, 2015

(65) Prior Publication Data
US 2016/0256556 A1     Sep. 8, 2016

(30) Foreign Application Priority Data

Oct. 8, 2013  (JP) .............................. JP2013-211308
Apr. 3, 2014  (JP) .............................. JP2014-077134

(51) Int. Cl.
| | | |
|---|---|---|
| *A23L 27/21* | (2016.01) | |
| *A61K 31/202* | (2006.01) | |
| *A61K 47/34* | (2017.01) | |
| *A21D 2/16* | (2006.01) | |
| *A61Q 19/00* | (2006.01) | |
| *A23L 2/56* | (2006.01) | |
| *A23D 9/013* | (2006.01) | |
| *A23C 9/13* | (2006.01) | |
| *A23F 5/40* | (2006.01) | |
| *A61K 8/36* | (2006.01) | |
| *A61K 8/64* | (2006.01) | |
| *A23G 9/32* | (2006.01) | |
| *A23G 9/44* | (2006.01) | |
| *A23G 9/52* | (2006.01) | |
| *A23D 9/007* | (2006.01) | |
| *A23L 27/00* | (2016.01) | |
| *A23L 33/115* | (2016.01) | |
| *A61K 8/72* | (2006.01) | |
| *A61K 47/14* | (2017.01) | |

(52) U.S. Cl.
CPC .............. *A61K 47/34* (2013.01); *A21D 2/16* (2013.01); *A23C 9/1315* (2013.01); *A23D 9/007* (2013.01); *A23D 9/013* (2013.01); *A23F 5/405* (2013.01); *A23G 9/32* (2013.01); *A23G 9/327* (2013.01); *A23G 9/44* (2013.01); *A23G 9/52* (2013.01); *A23L 2/56* (2013.01); *A23L 27/21* (2016.08); *A23L 27/84* (2016.08); *A23L 27/88* (2016.08); *A23L 33/115* (2016.08); *A61K 8/361* (2013.01); *A61K 8/64* (2013.01); *A61K 8/72* (2013.01); *A61K 31/202* (2013.01); *A61K 47/14* (2013.01); *A61Q 19/00* (2013.01); *A23V 2002/00* (2013.01); *A61K 2800/40* (2013.01)

(58) Field of Classification Search
CPC .......... A23L 27/80; A23L 27/88; A23L 17/20; A23L 27/21; A61K 31/202
See application file for complete search history.

(56) References Cited

U.S. PATENT DOCUMENTS

| | | | | |
|---|---|---|---|---|
| 3,687,721 | A | * | 8/1972 | Kimon ................... D06M 7/00 428/394 |
| 5,223,285 | A | | 6/1993 | DeMichele et al. |
| 5,674,475 | A | * | 10/1997 | Dahms ..................... A61K 8/85 424/59 |
| 7,718,709 | B2 | * | 5/2010 | Ishikawa .............. A23C 9/1315 516/73 |
| 2004/0029777 | A1 | | 2/2004 | Ando et al. |

(Continued)

FOREIGN PATENT DOCUMENTS

| | | |
|---|---|---|
| CN | 101579066 A | 11/2009 |
| CN | 102202739 A | 9/2011 |

(Continued)

OTHER PUBLICATIONS

Howard LeWine, M.D., "Fish oil: friend or foe?" Harvard Health Blog—https://www.health.harvard.edu/blog; Jul. 12, 2013: 2 pages).*
The Herbarie (Emulsifiers with HLB Values https://web.archive.org/web/20111114033552/https://www.theherbarie.com/files/resource-center/formulating/Emulsifiers_HLB_Values.pdf) (Year: 2011).*
Yamamoto et al. (Journal of Oleo Science (Jun. 2014); 63(9):893-901). (Year: 2014).*

(Continued)

*Primary Examiner* — Jeffrey S Lundgren
*Assistant Examiner* — Chris E Simmons
(74) *Attorney, Agent, or Firm* — Birch, Stewart, Kolasch & Birch, LLP

(57) ABSTRACT

A flavor improver for a polyunsaturated fatty acid-containing fat or oil, containing a basic peptide; and a polyunsaturated fatty acid-containing fat or oil composition, containing a fat or oil containing a polyunsaturated fatty acid having 18 or more carbon atoms and two more double bonds, a basic amino acid and/or a basic peptide, and an emulsifying agent. The flavor improver for a polyunsaturated fatty acid-containing fat or oil and the polyunsaturated fatty acid-containing fat or oil composition of the present invention can suppress the generation of unpleasant taste and flavor from the polyunsaturated fatty acid over a long time period.

17 Claims, No Drawings

(56) References Cited

U.S. PATENT DOCUMENTS

| | | | |
|---|---|---|---|
| 2005/0085604 A1* | 4/2005 | Handa | A61L 15/18 |
| | | | 526/227 |
| 2006/0165735 A1* | 7/2006 | Abril | A23D 7/003 |
| | | | 424/401 |
| 2007/0218182 A1 | 9/2007 | Schneider et al. | |
| 2010/0008885 A1 | 1/2010 | Daly et al. | |
| 2010/0323084 A1 | 12/2010 | Kamegai et al. | |
| 2011/0269849 A1* | 11/2011 | Yao | A01N 25/04 |
| | | | 514/773 |
| 2011/0305771 A1 | 12/2011 | Sampalis | |
| 2013/0102673 A1* | 4/2013 | Bouwer | A23D 9/06 |
| | | | 514/560 |
| 2013/0236561 A1 | 9/2013 | Meyer et al. | |
| 2013/0303614 A1 | 11/2013 | Kanehiro et al. | |
| 2015/0079261 A1 | 3/2015 | Matsuda | |

FOREIGN PATENT DOCUMENTS

| | | |
|---|---|---|
| CN | 102461726 A | 5/2012 |
| DE | 202007013532 U1 | 12/2007 |
| EP | 1712540 A1 | 10/2006 |
| JP | 2-23855 A | 1/1990 |
| JP | 5-140584 A | 6/1993 |
| JP | 5-287294 A | 11/1993 |
| JP | 7-107938 A | 4/1995 |
| JP | 7-227227 A | 8/1995 |
| JP | 8-154576 A | 8/1996 |
| JP | 8-302382 A | 11/1996 |
| JP | 9-111237 A | 4/1997 |
| JP | 9-263784 A | 10/1997 |
| JP | 10-140178 A | 5/1998 |
| JP | 11-228381 A | 8/1999 |
| JP | 2001-78702 A | 3/2001 |
| JP | 2001-192326 A | 7/2001 |
| JP | 2003-306690 A | 10/2003 |
| JP | 2005-185234 A | 7/2005 |
| JP | 2005-522488 A | 7/2005 |
| JP | 2006-271276 A | 10/2006 |
| JP | 2007-23009 A | 2/2007 |
| JP | 2007-70329 A | 3/2007 |
| JP | 2007-143432 A | 6/2007 |
| JP | 2007-516711 A | 6/2007 |
| JP | 2007-169192 A | 7/2007 |
| JP | 2008-290968 A | 12/2008 |
| JP | 2009-108065 A | 5/2009 |
| JP | 2009-171987 A | 8/2009 |
| JP | 4387440 B1 | 12/2009 |
| JP | 2011-156227 A | 8/2011 |
| JP | 2012-1640 A | 1/2012 |
| JP | 2013-79278 A | 5/2013 |
| JP | 2013-521004 A | 6/2013 |
| JP | 2013-147636 A | 8/2013 |
| JP | 2013-184980 A | 9/2013 |
| WO | WO 2007/075632 A2 | 7/2007 |
| WO | WO 2009/101972 A1 | 8/2009 |
| WO | WO 2012/063820 A1 | 5/2012 |
| WO | WO 2013/147132 A1 | 10/2013 |

OTHER PUBLICATIONS

Liu et al. (Journal of Food Quality 34 (2011) 64-73). (Year: 2011).*
"Tables of Food Composition in Japan," Chapter 2, 5th Edition and Supplement Standard, Jan. 24, 2005, retrieved from URL:http://www.mext.go.jp/b_menu/shingi/gijyutu/gijyutu3/toushin/05031802/002/014.pdf, 2 pages.
Ishihara et al., "Effects of Soybean Peptide on Suppression of Body Fat Accumulation during Endurance Swimming in Mice," Report of the Soy Protein Research Committee, vol. 17, 1996, pp. 94-97.
Japanese Office Action for Japanese Application No. 2013-211308, dated Jun. 22, 2017.
International Search Report (Form PCT/ISA/210), dated Jan. 20, 2015, for International Application No. PCT/JP2014/076767.
Extended European Search Report, dated Mar. 23, 2017, for European Application No. 14851739.4.
Endo et al., "Suppression of Fishy Odor in Sardine Meat," Nippon Shokuhin Kogyo Gakkaishi, vol. 36, No. 7, 1989, pp. 563-568, along with an English abstract.
European Office Action for European Application No. 14851739.4, dated Jun. 7, 2019.
European Office Action for Appl. No. 14 851 739.4 dated Jun. 17, 2020.
European Office Action for European Application No. 14851739.4, dated Nov. 20, 2020.

* cited by examiner

OIL/FAT COMPOSITION CONTAINING POLYUNSATURATED FATTY ACID

TECHNICAL FIELD

The present invention relates to a polyunsaturated fatty acid-containing fat or oil composition. More specifically, the present invention relates to a composition containing a fat or oil containing a polyunsaturated fatty acid, an emulsion composition or powder composition of the composition, foodstuff, a pharmaceutical composition, or cosmetics containing these compositions, and a method of reducing an off-flavor of a polyunsaturated fatty acid-containing fat or oil. In addition, the present invention relates to a flavor improver for a polyunsaturated fatty acid-containing fat or oil. More specifically, the present invention relates to a flavor improver for a fat or oil containing a polyunsaturated fatty acid, a composition containing the flavor improver, foodstuff, a pharmaceutical composition, or cosmetics containing the flavor improver or composition, and a method for improving flavor of a polyunsaturated fatty acid-containing fat or oil.

BACKGROUND ART

Polyunsaturated fatty acids contained in fish oils or the like, especially docosahexaenoic acid (DHA) and eicosapentaenoic acid (EPA) are substances having an action of physiological activity, such as an action of lowering blood neutral fats, an action of controlling blood pressure, activation of immune functions, amelioration of allergic symptoms, prevention of dementia, an anti-inflammatory action, or improvement in learning functions. Also, among linoleic acids contained in fats and oil derived from plant seeds or dairy products, conjugated linoleic acid is a substance having an action of physiological activity, such as an action of lowering body fats, an anti-fatigue action, enhancement of muscle strength, suppression of arteriosclerosis, or amelioration in allergic symptoms. This polyunsaturated fatty acid can hardly be biosynthesized in a live body, so that it is necessary to incorporate the polyunsaturated fatty acid as an essential fatty acid extracorporeally.

On the other hand, while these polyunsaturated fatty acids are being tried to be ingested by adding to various process foods, oxidation takes place with the passage of time, thereby resulting in generation of unpleasant taste or flavor. This unpleasant taste or flavor is called as "back odor (off-flavor)" and various studies have been made to suppress the generation of the off-flavor, or improve flavor.

For example, studies are made on combination of compounds that are conventionally used alone as an antioxidant or deodorant. Patent Publication 1 discloses a fish oil off-flavor suppressing agent in which 1 to 20% by weight of a tea extract, 80 to 98.9% by weight of tocopherol containing δ-tocopherol in a specified amount, and 0.1 to 5% by weight of ascorbic acid and/or its fatty acid ester are used in combination; and Patent Publication 2 discloses an antioxidant of DHA, in which tocopherol, L-ascorbate fatty acid ester, and a tea extract are used in combination. These publications also describe that an emulsifying agent is further combined to emulsify or disperse each of the components.

In addition, Patent Publication 3 describes that off-flavor of a fat or oil can be suppressed by including L-ascorbate ester in a fat or oil containing a polyunsaturated fatty acid such as DHA in an amount of from 100 to 2000 ppm. In that case, in a case where the L-ascorbate ester is a stearate ester or palmitate ester, the publication discloses that tocopherol is further contained in an amount of from 20 to 200 ppm and/or lecithin is further contained in an amount of from 0.01 to 2%. Patent Publication 4 discloses that an off-flavor of the polyunsaturated fatty acid-containing fat or oil can be suppressed by including 6-tocopherol in an amount of 1,600 ppm or more, and the publication describes that the effects may be enhanced by adding thereto L-ascorbate ester in an amount of 100 ppm or more.

On the other hand, Patent Publication 5 discloses an emulsion composition containing:
a natural oil containing DHA or EPA,
a polyglycerol fatty acid ester (fatty acid moiety having from 12 to 20 carbon atoms) having an HLB of 10 or more, alone or a mixture of the polyglycerol fatty acid ester with a sucrose fatty acid ester (fatty acid moiety having from 12 to 20 carbon atoms) and/or with lecithin, as a component capable of being emulsified with the natural oil,
an antioxidant, and
a hydrophilic medium of a polyhydric alcohol or a water-containing polyhydric alcohol
in combination, to provide as an over composition that is stable against oxidation, has no generation of odor, and is capable of being stored for a long time period. In this publication, the antioxidant includes ascorbic acids and catechin as preferred examples. In addition, Patent Publication 6 describes that oxidation stability of fats or oils can be remarkably improved by adding a polyalcohol-based emulsifying agent, especially a monoglyceride, to a fish oil or the like.

Further, Patent Publication 7 discloses a method for purification including efficiently performing deodorization and decoloration by allowing a fish oil to contact under a reduced pressure with a synthetic adsorbent, an ion-exchange resin, or the like. In addition, Patent Publication 8 discloses a method of stabilizing an emulsion state by allowing vitamin B's to be present upon mixing a fat emulsion with an injection of saccharides, amino acids, electrolytes, and vitamins, and the fat emulsion includes vegetable oils and fish oils.

As described above, there are numerous reports on techniques of suppressing off-flavor of a polyunsaturated fatty acid-containing fat or oil from fish oil or the like or providing a stable emulsion state by using a conventional antioxidant or deodorant.

Meanwhile, Patent Publication 9 discloses that a bad odor can be reduced by allowing a specified basic amino acid or a salt thereof to react with an unsaturated aldehyde such as nonenal, hexenal, or nonadienal to form an imine compound to make it non-volatile.

In addition, Patent Publication 10 discloses a method of removing an aldehyde which is causative of undesired taste or smell by allowing an edible oil such as fish oil to contact with an amino acid and an adsorbent from in-oil. The publication describes that the amino acid includes lysine, cysteine, and arginine, and that the amino acid and the aldehyde are allowed to react, and the reaction product is removed with an adsorbent. Patent Publication 11 discloses a method for reducing anisidine value by allowing an oil to contact with an amino acid.

PRIOR ART REFERENCES

Patent Publications

Patent Publication 1: Japanese Patent Laid-Open No. Hei-5-287294

Patent Publication 2: Japanese Patent Laid-Open No. Hei-9-111237
Patent Publication 3: Japanese Patent Laid-Open No. Hei-5-140584
Patent Publication 4: Japanese Patent Laid-Open No. Hei-9-263784
Patent Publication 5: Japanese Patent Laid-Open No. Hei-7-227227
Patent Publication 6: Japanese Patent Laid-Open No. Hei-10-140178
Patent Publication 7: Japanese Patent Laid-Open No. Hei-8-302382
Patent Publication 8: Japanese Patent Laid-Open No. 2008-290968
Patent Publication 9: Japanese Patent Laid-Open No. 2011-156227
Patent Publication 10: Japanese Unexamined Patent Publication No. 2013-521004
Patent Publication 11: WO 2007/075632

SUMMARY OF THE INVENTION

Problems to be Solved by the Invention

However, the conventionally proposed techniques have certain outcome, they are not necessarily satisfactory such as off-flavor is generated due to long-term storage. Therefore, the development of a composition having even more suppressed off-flavor of a polyunsaturated fatty acid-containing fat or oil, or materials that improve flavor of a polyunsaturated fatty acid-containing fat or oil has been desired.

An object of the present invention is to provide a flavor improver capable of improving a flavor of a polyunsaturated fatty acid-containing fat or oil for a long time period, a composition containing the flavor improver, foodstuff, a pharmaceutical composition or cosmetics containing the flavor improver or the composition, and a method for improving flavor of a polyunsaturated fatty acid-containing fat or oil.

In addition, an object of the present invention is to provide a polyunsaturated fatty acid-containing fat or oil composition in which off-flavor of the polyunsaturated fatty acid-containing fat or oil is suppressed for a long time period, an emulsion composition or powdery composition of the composition, and foodstuff, a pharmaceutical composition, or cosmetics containing these compositions, and a method for reducing off-flavor of a polyunsaturated fatty acid-containing fat or oil.

Means to Solve the Problems

The present invention relates to the following [1] to [22]:
[1] A flavor improver for a polyunsaturated fatty acid-containing fat or oil, containing a basic peptide.
[2] A polyunsaturated fatty acid-containing fat or oil composition, containing a fat or oil containing a polyunsaturated fatty acid and a basic peptide.
[3] A polyunsaturated fatty acid-containing fat or oil composition, containing a fat or oil containing a polyunsaturated fatty acid having 18 or more carbon atoms and two or more double bonds, a basic amino acid and/or a basic peptide, and an emulsifying agent.
[4] An emulsion composition of a polyunsaturated fatty acid-containing fat or oil, prepared by emulsifying the fat or oil composition as defined in the above [3].
[5] A powdery composition of a polyunsaturated fatty acid-containing fat or oil, prepared by powdering the fat or oil composition as defined in the above [3], or the emulsion composition as defined in the above [4].
[6] Foodstuff containing the flavor improver as defined in the above [1] or the composition as defined in any one of the above [2] to [5].
[7] A pharmaceutical composition containing the flavor improver as defined in the above [1] or the composition as defined in any one of the above [2] to [5].
[8] Cosmetics containing the flavor improver as defined in the above [1] or the composition as defined in any one of the above [2] to [5].
[9] Foodstuff prepared by blending foodstuff containing a fat or oil containing a polyunsaturated fatty acid with a basic peptide.
[10] A pharmaceutical composition prepared by blending a pharmaceutical composition containing a fat or oil containing a polyunsaturated fatty acid with a basic peptide.
[11] Cosmetics prepared by blending cosmetics containing a fat or oil containing a polyunsaturated fatty acid with a basic peptide.
[12] Foodstuff prepared by blending foodstuff containing a fat or oil containing a polyunsaturated fatty acid and an emulsifying agent with a basic amino acid and/or a basic peptide.
[13] A pharmaceutical composition prepared by blending a pharmaceutical composition containing a fat or oil containing a polyunsaturated fatty acid and an emulsifying agent with a basic amino acid and/or a basic peptide.
[14] Cosmetics prepared by blending cosmetics containing a fat or oil containing a polyunsaturated fatty acid and an emulsifying agent with a basic amino acid and/or a basic peptide.
[15] A method for reducing an off-flavor of a polyunsaturated fatty acid-containing fat or oil, characterized by the inclusion of an emulsifying agent together with a basic amino acid and/or a basic peptide, in a fat or oil containing a polyunsaturated fatty acid having 18 or more carbon atoms and two or more double bonds.
[16] A method for improving a flavor of a polyunsaturated fatty acid-containing fat or oil, characterized by the inclusion of a basic peptide in a fat or oil containing a polyunsaturated fatty acid having 18 or more carbon atoms and two or more double bonds.
[17] A basic amino acid and/or a basic peptide, for reducing an off-flavor of a polyunsaturated fatty acid-containing fat or oil.
[18] A basic peptide for improving a flavor of a polyunsaturated fatty acid-containing fat or oil.
[19] Use of a basic amino acid and/or a basic peptide, for reducing an off-flavor of a polyunsaturated fatty acid-containing fat or oil.
[20] Use of a basic peptide for improving a flavor of a polyunsaturated fatty acid-containing fat or oil.
[21] Use of a basic amino acid and/or a basic peptide, in the preparation of a composition for reducing an off-flavor of a polyunsaturated fatty acid-containing fat or oil.
[22] Use of a basic peptide in the preparation of a composition for improving a flavor of a polyunsaturated fatty acid-containing fat or oil.

Effects of the Invention

The flavor improver for a polyunsaturated fatty acid-containing fat or oil of the present invention and the polyunsaturated fatty acid-containing fat or oil composition of the present invention exhibit some excellent effects that the generation of unpleasant taste and flavor from the polyunsaturated fatty acid-containing fat or oil can be suppressed over a long time period.

MODES FOR CARRYING OUT THE INVENTION

While polyunsaturated fatty acids, especially docosahexaenoic acid (DHA) or eicosapentaenoic acid (EPA), linoleic acid (especially conjugated linoleic acid) have excellent actions of physiological activity, the polyunsaturated fatty acids are oxidized with the passage of time to cause unpleasant taste or flavor, a so-called off-flavor. This off-flavor is complicated in the components and generation mechanisms, so that the suppression mechanisms therefor have not yet been satisfactorily elucidated. However, in the present invention, surprisingly, when a polyunsaturated fatty acid-containing fat or oil is mixed together with a basic peptide or with a basic amino acid and/or a basic peptide as well as an emulsifying agent, respectively, it has been found that the generation of off-flavor is suppressed over a long time period. Although the detailed mechanisms therefor are not certain, it is assumed as follows. A terminal carbonyl group of the bad odor component generated from the above polyunsaturated fatty acid-containing fat or oil is allowed to react with an amino group of a basic amino acid and/or a basic peptide to form an imine compound to produce a polymer, thereby the bad odor component is made non-volatile, and further when an emulsifying agent is present, the compound that is made non-volatile is dispersed in a liquid with the emulsifying agent, thereby even more suppressing volatilization. In addition, it is considered that the emulsifying agent improves the compatibility with the basic amino acid or basic peptide which is hardly soluble to a fat or oil, whereby the contact efficiency with the bad odor component is improved, thereby accelerating the formation of an imine compound, thereby even more exhibiting the above effects.

The flavor improver for a polyunsaturated fatty acid-containing fat or oil of the present invention is characterized by the inclusion of a basic peptide. Here, in the subsequent descriptions, the flavor improver for a polyunsaturated fatty acid-containing fat or oil of the present invention may be simply referred to as the flavor improver of the present invention.

The basic peptide in the flavor improver of the present invention refers to a peptide of which isoelectric point is on an alkaline side than the physiological conditions, the peptide including a basic amino acid as the constituting amino acids. The basic amino acid includes the above amino acids, including preferably one or more members selected from the group consisting of lysine, arginine, and histidine. The degree of polymerization of the peptide is usually 2 or more, and preferably 5 or more, and preferably 200 or less, more preferably 100 or less, and even more preferably 60 or less. The preferred basic peptides include polylysine, polyarginine, polyhistidine, histone, and protamine.

A basic peptide that is synthesized by a known method may be used, or a commercially available basic peptide can be used.

In the present invention, the basic peptide may be used alone or a combination of two or more kinds, and the basic peptide can be used in combination with other peptides or amino acids within the range that would not impair the effects of the present invention.

The flavor improver of the present invention is not particularly limited in other components, so long as the flavor improver contains the basic peptide. The content of the basic peptide in the flavor improver of the present invention is preferably 0.1% by weight or more, more preferably 1.0% by weight or more, and even more preferably substantially 100% by weight, so that the flavor improver of the present invention may only consist of the basic peptide.

Since the flavor improver of the present invention can suppress the generation of unpleasant taste and flavor from a polyunsaturated fatty acid-containing fat or oil over a long time period, the present invention further provides a polyunsaturated fatty acid-containing fat or oil composition containing a flavor improver of the present invention.

The polyunsaturated fatty acid-containing fat or oil composition of the present invention include:
an embodiment of containing a flavor improver of the present invention (Embodiment 1); and
an embodiment of containing a polyunsaturated fatty acid-containing fat or oil with a basic amino acid and/or a basic peptide, and an emulsifying agent (Embodiment 2).

Here, in the subsequent descriptions, the polyunsaturated fatty acid-containing fat or oil composition of the present invention may be simply referred to as a fat or oil composition of the present invention.

The polyunsaturated fatty acid-containing fat or oil in the present invention refers to a fat or oil containing a polyunsaturated fatty acid, and the polyunsaturated fatty acid-containing fat or oil is not particularly limited, so long as it contains a polyunsaturated fatty acid. The polyunsaturated fatty acid in the present invention collectively refers to a fatty acid having 18 or more carbon atoms and having two or more double bonds in the molecule, or a compound having the fatty acid as a constituent, which is roughly classified to n-3 compounds or n-6 compounds depending upon the positions of the double bonds. The n-3 fatty acid includes fatty acids such as α-linolenic acid, eicosapentaenoic acid (EPA), docosahexaenoic acid (DHA), and docasapentaenoic acid (DPA), and the n-6 fatty acid includes fatty acids such as linoleic acid, γ-linolenic acid, and arachidonic acid.

These fatty acids can also be utilized in the form of derivatives thereof. For example, the fatty acids may be salts of fatty acids, or esters with glycerol or ethanol, or constituents of phospholipids. Among them, a triglyceride which is a glyceryl ester is preferably used because it can be conveniently used.

Naturally occurring vegetable oils, fish oils, extraction oils or fats or oils from animal or plant planktons, or fats or oils obtained synthetically contain a polyunsaturated fatty acid in the form of triglyceride, which can be directly used in the present invention. These may be appropriately selected depending upon the purposes. Since those having a higher content of the polyunsaturated fatty acids are more desired if some physiological effects are expected, the synthetic fat or oil, and fish oils and extraction oils or fats or oils from plant planktons can be preferably utilized.

Since the higher physiological effects are desired, the content of the polyunsaturated fatty acid in these fats and oils is preferably 1% by weight or more, more preferably 5% by weight or more, and even more preferably 10% by weight or more, and preferably 99% by weight or less, and more preferably 95% by weight or less. The content of the polyunsaturated fatty acid as used herein means a total content in a case of containing plural polyunsaturated fatty acids. Here, fat or oils having a content of a polyunsaturated fatty acid of from 20 to 90% by weight or so are commercially available, and these can be also used. In addition, a fat or oil or a synthetic oil derived from other raw materials may be added to a naturally occurring extraction fat or oil to adjust the content of the polyunsaturated fatty acid.

The polyunsaturated fatty acid-containing fat or oil composition of Embodiment 1 is not particularly limited, so long as the above polyunsaturated fatty acid-containing fat or oil or the flavor improver of the present invention is contained. It is preferable that the polyunsaturated fatty acid contains fatty acids having 18 or more carbon atoms and having two or more double bonds in the molecule.

The content of the polyunsaturated fatty acid in the fat or oil composition of Embodiment 1 is preferably 0.1% by weight or more, more preferably 1% by weight or more, and even more preferably 5% by weight or more, and preferably 99% by weight or less, and more preferably 95% by weight or less.

The content of the polyunsaturated fatty acid-containing fat or oil in the fat or oil composition of Embodiment 1 is preferably 0.1% by weight or more, more preferably 1% by weight or more, and even more preferably 6% by weight or more, and preferably 99.9% by weight or less, and more preferably 99% by weight or less.

In addition, the content of the flavor improver of the present invention in the fat or oil composition of Embodiment 1 is not particularly limited, so long as the content of the basic peptide would be as follows. The content of the basic peptide in the fat or oil composition of Embodiment 1 is preferably 0.001% by weight or more, more preferably 0.01% by weight or more, and even more preferably 0.1% by weight or more, and preferably 50% by weight or less, more preferably 20% by weight or less, even more preferably 10% by weight or less, and even more preferably 5% by weight or less. The content of the basic peptide as referred to herein means a total content in a case where plural basic peptides are contained.

The weight ratio of the polyunsaturated fatty acid to the basic peptide in the fat or oil composition of Embodiment 1 (the polyunsaturated fatty acid/the basic peptide) is preferably from 0.005/1 to 10000/1, and more preferably from 0.1/1 to 5000/1.

The fat or oil composition of Embodiment 1 can contain an emulsifying agent, in addition to the polyunsaturated fatty acid-containing fat or oil and the basic peptide, from the viewpoint of dispersing the basic peptide.

As the emulsifying agent in Embodiment 1, a known emulsifying agent can be used. For example, one or more members selected from the group consisting of glycerol fatty acid esters, sucrose fatty acid esters, propylene glycol fatty acid esters, phospholipids, and polyoxyethylene sorbitan fatty acid esters are preferred, among which glycerol fatty acid esters are more preferred because the polyunsaturated fatty acid can be stably kept.

The content of the emulsifying agent in the fat or oil composition of Embodiment 1 is preferably 10% by weight or less, more preferably 7.5% by weight or less, and more preferably 5% by weight or less. The content of the emulsifying agent as referred to herein means a total content in a case where plural emulsifying agents are contained.

In addition, the polyunsaturated fatty acid-containing fat or oil composition of Embodiment 2 contains a fat or oil containing a polyunsaturated fatty acid having 18 or more carbon atoms and having two or more double bonds, among the polyunsaturated fatty acid-containing fats or oils mentioned above, and a basic amino acid and/or a basic peptide, and an emulsifying agent.

The content of the polyunsaturated fatty acid in the fat or oil composition of Embodiment 2 is preferably 0.1% by weight or more, more preferably 1% by weight or more, and even more preferably 5% by weight or more, and preferably 99% by weight or less, and more preferably 95% by weight or less.

The content of the polyunsaturated fatty acid-containing fat or oil in the fat or oil composition of Embodiment 2 is preferably 0.1% by weight or more, more preferably 1% by weight or more, and even more preferably 6% by weight or more, and preferably 99.9% by weight or less, and more preferably 99% by weight or less.

The basic amino acid in the fat or oil composition of Embodiment 2 refers to an amino acid of which isoelectric point is on an alkaline side than physiological conditions, which includes, for example, lysine, arginine, histidine, ornithine, carnitine, creatine, and salts thereof, and the like. Among them, one or more members selected from the group consisting of lysine, arginine, histidine, and hydrochlorides thereof are preferred, from the viewpoint of availability.

The basic peptide in the fat or oil composition of Embodiment 2 refers to a peptide of which isoelectric point is on an alkaline side than physiological conditions, the peptide including as a constituting amino acid a basic amino acid. The basic amino acid includes amino acids mentioned above, and preferably including one or more members selected from the group consisting of lysine, arginine, and histidine. The degree of polymerization of the peptide includes those peptides consisting of usually from 5 to 100, amino acids, and preferably 5 to 60 amino acids. Preferred basic peptides include polylysine, polyarginine, polyhistidine, histone, and protamine.

A basic peptide synthesized according to a known method may be used, or a commercially available product can be used.

In the fat or oil composition of Embodiment 2, the basic amino acid may be used alone or in a combination of two or more kinds, and the basic peptide may be used alone or in a combination of two or more kinds, or a basic amino acid and a basic peptide may be used in combination, and the combinations thereof are not particularly limited.

The content of the basic amino acid and/or the basic peptide in the fat or oil composition of Embodiment 2 is preferably 0.001% by weight or more, more preferably 0.01% by weight or more, and even more preferably 0.1% by weight or more, and preferably 20% by weight or less, more preferably 10% by weight or less, and even more preferably 5% by weight or less. The content of the basic amino acid and/or the basic peptide as used herein means a total content in a case where plural basic amino acids and basic peptides are contained.

In addition, the weight ratio of the polyunsaturated fatty acid to the basic amino acid and/or the basic peptide [the polyunsaturated fatty acid/(the basic amino acid+the basic peptide)] is preferably from 90/0.01 to 5/1, and more preferably 30/0.01 to 9/1.

As the emulsifying agent in the fat or oil composition of Embodiment 2, a known emulsifying agent can be used. The emulsifying agent includes nonionic emulsifying agents such as glycerol fatty acid esters, organic acids monoglyceride, monoglyceride derivatives, sorbitan fatty acid esters, propylene glycol fatty acid esters, polyethylene glycol fatty acid esters, sucrose fatty acid esters, SAIB, phospholipids such as lecithin and enzymatically degraded lecithin, saponin, *Quillaya* extracts, *Yucca* extracts, polyoxyethylene castor oil, polyoxyethylene hydrogenated castor oil, polyoxyethylene sorbitan fatty acid esters, polyoxyethylene-polyoxypropylene glycols, polyoxyethylene derivatives, glycerol alkyl ethers, polyglycerol alkyl ethers, polyoxyethylene alkyl ethers, polyoxyethylene-polyoxypropylene alkyl ethers, and alkyl glycosides; anionic emulsifying agents such as alkyl sulfonic acids, alkylbenzenesulfonic acids, polyoxyethylene alkyl ether sulfonic acids, N-acyl-L-glutamic acid, fatty acids, and salts thereof; cationic surfactants such as alkyltrimethylammonium, alkylammonium, and salts thereof; and amphoteric emulsifying agents such as N-acyl-L-arginine and betaine. Among them, one or more members selected from the group consisting of glycerol fatty acid esters, sucrose fatty acid esters, propylene glycol fatty acid esters, and phospholipids are preferred, and glycerol fatty acid esters are more preferred, because the polyunsaturated fatty acid can be stably kept.

The glycerol fatty acid ester is obtained by esterification formed between glycerol and a fatty acid, and includes monoglycerol fatty acid esters and polyglycerol fatty acid esters, depending upon the degrees of polymerization of glycerol.

The glycerol is not particularly limited, and any of monoglycerols, diglycerols, polyglycerols, and the like can be used. In addition, the polyglycerol is preferably a polyglycerol of which hydroxyl value is 1,200 or less, and primary hydroxyl groups of all the hydroxyl groups is 50% by number or more. Among them, it is desired that the polyglycerol of which primary hydroxyl group is preferably 55% by number or more, and more preferably 60% by number or more, from the viewpoint of the effects on increasing compatibility between the polyunsaturated fatty acid-containing fat or oil and the basic amino acid and/or the basic peptide, and further the upper limit is, but not particularly limited thereto, 90% by number or less, preferably 80% by number or less, and more preferably 70% by number or less, in order to maximally exhibit the effects thereof. In addition, the hydroxyl value is preferably 1,100 or less, and more preferably 1,000 or less, from the viewpoint of being capable of adjusting hydrophilicity (HLB) of the polyglycerol fatty acid esters depending upon the applications. In addition, the hydroxyl value is preferably 770 or more, from the viewpoint of workability and easiness in esterification with fatty acids.

The proportion of the primary hydroxyl groups of all the hydroxyl groups is determined by using a method of determining nuclear magnetic resonance spectrum (NMR) against carbon atoms. In addition, the hydroxyl value can be determined by a known method in the art.

The nuclear magnetic resonance spectrum (NMR) against carbon atoms can be determined as follows. Five-hundred milligrams of polyglycerol is dissolved in 2.8 mL of deuterated water, and the mixture is filtered, and $^{13}$C-NMR (125 MHz) spectrum is obtained by gated decoupling. The peak intensity according the method of gate decoupled determination is proportional to the number of carbon atoms. The $^{13}$C chemical shifts showing the existence of the primary hydroxyl groups and the secondary primary groups are at near 63 ppm for methylene carbon ($CH_2OH$), and at near 71 ppm for methyne carbon (CHOH), respectively, and the existing ratio of the primary groups to the secondary groups is calculated according to analyses of each of two kinds of signal intensities. Here, since the methyne carbon (CHOH) showing a secondary hydroxyl group overlaps with the methylene carbon peaks further adjoining to the methyne carbon bonded to the methylene carbon showing a primary hydroxyl group, a value of an integral of the methyne carbon itself cannot be obtained, and the value of an integral is calculated from the signal intensity of methylene carbon ($CH_2$) adjoining the methyne carbon (CHOH) at near 74 ppm.

The method for preparing polyglycerol of the polyglycerol fatty acid ester used in the fat or oil composition of Embodiment 2 is not particularly limited. For example, the polyglycerol can be obtained by a known synthesis method, or fractional purification from a commercially available polyglycerol.

As the constituent fatty acid, which is another constituent of the glycerol fatty acid ester, a saturated or unsaturated fatty acid having the number of carbon atoms of preferably 10 or more, more preferably 12 or more, and even more preferably 14 or more is preferred, from the viewpoint of interfacial modification of the polyunsaturated fatty acid and the basic amino acid and/or the basic peptide. Specific examples of the saturated fatty acid include capric acid, lauric acid, myristic acid, pentadecylic acid, palmitic acid, margaric acid, stearic acid, nonadecanoic acid, arachidic acid, behenic acid, and isomers thereof, and the like. Specific examples of the unsaturated fatty acid include palmitoleic acid, oleic acid, vaccenic acid, linoleic acid, eicosadienoic acid, docosadienoic acid, linolenic acid, ricinoleic acid, arachidonic acid, erucic acid, and isomers thereof, condensates thereof, and isomers of the condensates, and the like. Among them, the unsaturated or saturated fatty acid preferably includes myristic acid, palmitic acid, stearic acid, oleic acid, ricinoleic acid, and isomers thereof, condensates thereof, and isomers of the condensates.

In addition, other fatty acids may be contained, within the range that would not impair the effects of the present invention. For example, other fatty acids include, in addition to caproic acid and caprylic acid, 12-hydroxystearic acid, 9-hydroxystearic acid, 10-hydroxystearic acid, hydrogenated castor oil fatty acid (fatty acids containing small amounts of stearic acid and palmitic acid besides 12-hydroxystearic acid), and the like.

The esterification reaction between glycerol and a fatty acid is not particularly limited so long as the esterification reaction is carried out by a general synthesis method. For example, the esterification reaction can be carried out according to a method described in Japanese Patent Laid-Open No. 2011-168716. Here, the glycerol fatty acid ester obtained can be further purified according to a known method as demanded upon use of the manufactured articles used.

The content of the glycerol fatty acid ester in the emulsifying agent is preferably 0.01% by weight or more, and more preferably 0.5% by weight or more, because it is preferable that the reaction product formed between the polyunsaturated fatty acid and the basic amino acid and/or the basic peptide can be stably kept. In addition, the content is preferably 1,100% by weight or less. The emulsifying agent of the present invention may consist of the glycerol fatty acid ester. The content of the glycerol fatty acid ester as used herein means a total content in a case where the emulsifying agent contains plural glycerol fatty acid esters.

In addition, it is preferable that one or more members of the emulsifying agents used in the fat or oil composition of Embodiment 2 have an HLB value of preferably less than 10, and more preferably from 9 to 1, from the viewpoint of improving compatibility between the basic amino acid and/or the basic peptide and the polyunsaturated fatty acid-containing fat or oil. The content of the emulsifying agent having the above HLB value is, but not particularly limited thereto, preferably 1% by weight or more, and more preferably 5% by weight or more, of the entire emulsifying agents, and the emulsifying agent may consist only of the emulsifying agent having the above HLB value. Here, in the present specification, the HLB value can be actually measured using known lipophilic surfactants and fats and oils, or the HLB value can be calculated by the following equation from the saponification value of the ester and the neutralization value of the fatty acids used.

$$HLB = 20 \times (1 - S/A)$$

wherein S: a saponification value, and A: a neutralization value of fatty acids.

In addition, the content of the emulsifying agent in the fat or oil composition of Embodiment 2 having an HLB value of less than 10 is preferably 0.001% by weight or more, more preferably 0.01% by weight or more, and even more preferably 0.1% by weight or more, and preferably 60% by weight or less, more preferably 40% by weight or less, and even more preferably 20% by weight or less. The content of the emulsifying agent having an HLB value of less than 10 as used herein means a total content of emulsifying agents having an HLB value of less than 10 in a case where plural emulsifying agents are contained.

The content of the emulsifying agent in the fat or oil composition of Embodiment 2 is preferably 0.001% by weight or more, more preferably 0.01% by weight or more, and even more preferably 0.1% by weight or more, and preferably 80% by weight or less, more preferably 70% by weight or less, and even more preferably 60% by weight or less. The content of the emulsifying agent as used herein means a total content in a case where plural emulsifying agents are contained.

In addition, the weight ratio of the polyunsaturated fatty acid to the emulsifying agent [the polyunsaturated fatty acid/the emulsifying agent] in the fat or oil composition of Embodiment 2 is preferably from 100/0.01 to 0.05/1, and more preferably from 100/1 to 0.1/1. The content of the emulsifying agent as used herein means a total content in a case where plural emulsifying agents are contained.

Also, the weight ratio of the polyunsaturated fatty acid to the emulsifying agent having an HLB value of less than 10 [the polyunsaturated fatty acid/the emulsifying agent] in the fat or oil composition of Embodiment 2 is preferably from 100/0.01 to 0.05/1, and more preferably from 100/1 to 0.2/1. The content of the emulsifying agent having an HLB value of less than 10 means a total content of the emulsifying agents having an HLB value of less than 10 in a case where plural emulsifying agents are contained.

In addition, the fat or oil composition of the present invention can further contain, in both Embodiment 1 and Embodiment 2, an antioxidant and/or an oxidation inhibitor, from the viewpoint of keeping the polyunsaturated fatty acid stable.

The antioxidant and/or the oxidation inhibitor is not particularly limited, and a known one is used, which includes, for example, tocopherols; polyphenols; dibutylhydroxytoluene (BHT); butylhydroxyanisole (BHA); gluconic acid, kojic acid, phytic acid, polyphosphoric acid, ferulic acid, ellagic acid, citric acid, ascorbic acid, isoascorbic acid, erythorbic acid, gallic acid, chlorogenic acid, quinic acid, nucleic acids or salts thereof or fatty acid esters; catechins; grape seed extracts, rosemary extracts, sunflower extracts, red bayberry extracts, Amla extracts, edible canna extracts, blueberry leaf extracts, Umbelliferae extracts, Hego-ginkgo leaf extracts, balsam extracts, cucumber extracts, parsley extracts, pomegranate extracts, enzymatically treated rutin, quercetin, resveratrol, ubiquinone, α-lipoic acid, and anthocyan; polyphenol-containing natural extracts such as tea extracts; carotenoids such as astaxanthin, lycopene, and lutein; licorice extracts, rapeseed extracts, sesame oil non-saponified products, γ-oryzanol, *Houttuynia cordata* extract extracts, hollyhock flower extracts, pimenta extracts, hesperidin, hesperetin, sesamolin, sesamol, chitin, chitosan, and the like. Among them, one or more members selected from the group consisting of tocopherol, catechins, and ascorbic acid can be used.

The content of the antioxidant and/or the antioxidant in the fat or oil composition of the present invention is preferably 0.001% by weight or more, more preferably 0.01% by weight or more, and even more preferably 0.1% by weight or more, and preferably 10% by weight or less, more preferably 5% by weight or less, and even more preferably 2% by weight or less. The content of the antioxidant and/or the antioxidant as used herein means a total content in a case where plural antioxidants and/or antioxidants are contained.

The fat or oil composition of the present invention can be used, in both Embodiment 1 and Embodiment 2, in combination with other useful components as other components than those mentioned above, within the range that would not impair the effects of the present invention, whereby the stability of the composition and the additional values can be can be improved. Such components, if exemplified, include sweeteners such as licorice extracts, saccharin sodium, and aspartame; polysaccharides such as gum arabic, pectin, carrageenan, Furcelleran, guar gum, locust bean gum, xanthan gum, alginic acid, methyl cellulose, oligosaccharides, dextrin, cyclodextrin, water-soluble dietary fibers, and non-water-soluble dietary fibers; colorants such as gardenia dyes, tomato dyes, Hematococcus algae dyes, Marigold dyes, carotenoid dyes, and Yellow No. 4, preservatives such as potassium sorbate, sodium benzoate, sodium acetate, and hinokithiol, sour flavoring such as citric acid and phytic acid, seasonings such as sodium inosinate and sodium glutamate, flavors such as citrus flavors, milk flavors, yogurt flavors, and masking flavors, buffers, pH adjusting agents, alkalizing agents such as sodium hydroxide and potassium hydroxide, defoaming agents, vitamins such as vitamin A, vitamin D, vitamin E, vitamin C, vitamin B group, and pantothenic acid, amino acids such as L-glycine, L-threonine, L-tryptophan, L-theanine, L-glutamate, minerals such as calcium, iron, zinc, copper, and magnesium, or salts thereof, functional materials such as sesamin, isoflavone, lactoferrin, lactulose, lactic acid bacteria, phytosterol, collagen, elastin, ceramide, chondroitin sulfate, N-acetylglucosamine, hyaluronic acid, placenta, squalene, curcumin, allyl sulfide, alliin, phosphatidyl serine, phosphatidyl choline, coumarin, royal jelly, propolis, Agaricus fungi powders, lingzhi mushroom powders, spirulina powders, chlorella powders, vegetative wasp extracts, mulberry leaf extracts, ginseng extracts, denshichi carrot extracts, and glycyrrithinic acid, acetylcholine esterase inhibitors such as galanthamine and rivastigmine donepezil, hyperlipemia improvers such as mevastatin, fenofibrate, and cholestimide, antihistamines such as diphenhydramine hydrochloride, chlorphenylamine maleate, ketotifen fumarate, and cetirizine hydrochloride, proteins such as milk serum proteins, whey peptides, egg peptides, soybean peptides, and enzymes, and the like. The contents of these components are not particularly limited, and can be appropriately set according to known techniques. In addition, the fat or oil composition of Embodiment 1 can contain, in addition to the other components mentioned above, water and alcohol, and the fat or oil composition of Embodiment 2 can contain, in addition to the other components mentioned above, a fat or oil not containing a polyunsaturated fatty acid having 18 or more carbon atoms and having two or more double bonds, respectively.

The alcohol includes monohydric alcohols and polyhydric alcohols. The monohydric alcohol include monohydric lower alcohols and monohydric higher alcohols. Concrete examples of the monohydric lower alcohols include, for example, ethanol, propanol, and butanol, and concrete examples of the monohydric higher alcohols include, for example, cetyl alcohol, and stearyl alcohol. Concrete examples of the polyhydric alcohol include, for example, ethylene glycol, propylene glycol, butylene glycol, glycerol, diglycerol, triglycerol, polyglycerol, sorbitol, xylitol, maltitol, lactitol, sorbitan, xylose, arabinose, mannose, lactose, sugar, coupling sugar, glucose, enzyme-saccharified syrup, acid saccharified syrup, maltose syrup, maltose, isomerized sugar, fructose, reduced maltose syrup, reduced starch saccharidization products, honey, fructose-glucose liquid sugar, and aqueous solutions thereof. These can be used alone or two or more kinds in combination, among them, the polyhydric alcohols are preferred, and propylene glycol, glycerol and reduced starch saccharidization products are more preferred, from the viewpoint of easiness in the production of the formulation, and stability. Here, the polyhydric alcohol as used herein means a compound having two or more hydroxyl group in one molecule.

The fat or oil composition of Embodiment 1 is not particularly limited in the preparation method thereof, so long as the fat or oil composition contains the polyunsaturated fatty acid-containing fat or oil and the basic peptide. In addition, the fat or oil composition of Embodiment 2 is not particularly limited in the preparation method thereof, so long as the fat or oil composition contains the polyunsaturated fatty acid-containing fat or oil, the basic amino acid and/or the basic peptide, and the emulsifying agent. Both the compositions of Embodiment 1 and Embodiment 2 can be prepared by, for example, mixing the above raw materials with an agitator, an emulsifier, or the like. For example, the agitator or emulsifier includes agitators equipped with agitation blades of propeller type, anchor type, paddle type, disk turbine type and the like, rotor-stator type emulsifiers, mill type emulsifiers, high-pressure nozzle-type emulsifiers, high-pressure collision-type emulsifiers, ultrasonic emulsifiers, membrane emulsifiers, microchannel emulsifiers, static mixers, powder dissolving machine, and the like. These agitators or emulsifiers can be used alone or in a combination of two or more kinds. Among them, paddle blade agitators, rotator-stator type emulsifiers, high-pressure nozzle-type emulsifiers, high-pressure collision-type emulsifiers can be preferably used from the viewpoint of high all-purposefulness.

Since the fat or oil composition of the present invention can suppress the generation of unpleasant taste or flavor from a polyunsaturated fatty acid for a long time period, the fat or oil composition is suitably used, for example, as foodstuff, a pharmaceutical composition, cosmetics, or raw materials thereof, in order to exhibit the action of physiological activity of the polyunsaturated fatty acid without showing any unpleasant taste or flavor.

The forms of the fat or oil composition are not particularly limited, so long as the fat or oil composition is in the form that can be ingested in the body or externally applied to skin or the like. The fat or oil composition of the present invention may be ingested directly, or ingested in the form of an emulsified product or a powdered product of the fat or oil composition of the present invention, or in the form of a powdered product obtained by further powdering the emulsion.

Specific forms of the fat or oil composition of Embodiment 1 of the present invention include, for example, in a case of a fat or oil composition, or an emulsified product of the composition, dry syrups, solutions (including suspension, emulsion, syrup, lemonade, or the like), and the like. In addition, in a case where the fat or oil composition is powdered, the forms include a powder, a fine powder, a fine granule, a granule, and the like. Among them, solutions and fine powders are preferred.

The fat or oil composition of Embodiment 1 of the present invention having the above form can be prepared by a conventional method, so long as the fat or oil composition contains the polyunsaturated fatty acid-containing fat or oil and the basic peptide. For example, in a case of solutions, the fat or oil composition can be prepared by mixing a polyunsaturated fatty acid-containing fat or oil with a basic peptide and optionally other additives sequentially.

The present invention also provides, as one of the embodiments of the fat or oil composition of the present invention, an emulsion composition prepared by emulsifying a fat or oil composition of Embodiment 2 of the present invention, or a powder composition obtained by powdering a fat or oil composition of Embodiment 2 of the present invention or the above emulsion composition. Here, the emulsion composition in the present invention is an oil-in-water composition.

The emulsion composition of the present invention is not particularly limited, so long as the fat or oil composition of Embodiment 2 of the present invention is emulsified. Accordingly, the emulsion composition of the present invention can contain, in addition to, a polyunsaturated fatty acid-containing fat or oil, a basic amino acid and/or a basic peptide, and an emulsifying agent, for example, water, an alcohol, or the like. Here, the polyunsaturated fatty acid-containing fat or oil, the basic amino acid and/or the basic peptide, and the emulsifying agent can be used in the same manner as in the fat or oil composition of Embodiment 2 of the present invention mentioned above. In addition, the content of water, an alcohol or the like can be, but not particularly limited to, appropriately set according to known techniques.

As the alcohol, the same ones as those alcohols which can be used in the fat or oil composition of Embodiment 1 mentioned above can be used.

The emulsion composition of the present invention can be prepared according to a known method. Specifically, an emulsion composition can be prepared by, for example, mixing an alcohol and/or water and an emulsifying agent, mixing a mixture obtained with a polyunsaturated fatty acid-containing fat or oil previously separately mixed with an emulsifying agent, thereafter mixing a mixture obtained with a basic amino acid and/or a basic peptide directly, or one previously added to water, and optionally other additives sequentially. Here, the basic amino acid and/or basic peptide may be dispersed in the polyunsaturated fatty acid-containing fat or oil. In addition, the order of adding these components are not particularly limited. Here, in the mixing of the above raw materials, an agitator or emulsifier that can be used upon the preparation of the above fat or oil composition may be suitably used.

The powder composition of the present invention is not particularly limited, so long as the fat or oil composition of Embodiment 2 of the present invention is directly powdered, or the emulsion composition of the present invention mentioned above is powdered. Accordingly, the powder composition of the present invention may further contain, in addition to the polyunsaturated fatty acid-containing fat or oil, the basic amino acid and/or the basic peptide, and the emulsifying agent, a known substance in the art needed for powdering, including, for example, an additive, such as a excipient, a binder, a disintegrating agent, a lubricant, a sweetener, a corrigent, a preservative, chelating agent, an antioxidant, a cooling agent, a coating agent, a stabilizer, a fluidizing agent, a thickening agent, a dissolution aid, a thickening agent, a buffer, a flavor, a colorant, an adsorbent, a wetting agent, a dampproof agent, an antistatic agent, a plasticizer, a defoaming agent, a foaming agent, a surfactant, or an emulsifying agent. Here, the polyunsaturated fatty acid-containing fat or oil, the basic amino acid and/or the basic peptide, and the emulsifying agent may be used in the same manner as in the fat or oil composition of Embodiment 2 of the present invention mentioned above. In addition, the content of the substance needed for powdering is not particularly limited, and can be properly set depending upon known techniques.

The powder composition of the present invention can be prepared in accordance with a known method. Specifically, the powder composition can be prepared by, for example, mixing an emulsifying agent with a polyunsaturated fatty acid-containing fat or oil, then with a basic amino acid and/or a basic peptide, and optionally other additives sequentially, and further in a case of further emulsification, after emulsification, mixing an additive such as an excipient, subjecting to spray-drying or lyophilization or the like. Here, a polyunsaturated fatty acid-containing fat or oil which is previously emulsified with an emulsifying agent may be also used.

Specific forms of the fat or oil composition of Embodiment 2 of the present invention include, for example, in a case of a fat or oil composition or an emulsion composition, dry syrups, solutions (including suspension, emulsion, syrup, lemonade, or the like), and the like. In addition, the forms of the powder composition include a powder, a fine powder, a fine granule, a granule, and the like. Among them, solutions and fine powders are preferred.

The fat or oil composition of the present invention, in both of Embodiment 1 and Embodiment 2 can be utilized without particular limitations depending upon the forms. The fat or oil composition can be used for exhibition or improvement in an action of physiological activity, including an action of lowering blood neutral fats, an action of controlling blood pressure, activation of immune functions, amelioration of allergic symptoms, prevention of dementia, an anti-inflammatory action, improvement in learning functions, an action of lowering body fats, an anti-fatigue action, enhancing action of muscle strength, or suppression of arteriosclerosis.

The amount of the fat or oil composition of the present invention used is properly set depending upon the forms, methods of use, use purposes, and age, body weight, and symptoms of subjects using the composition, and is not unconditionally determined. For example, in a case where the fat or oil composition is orally ingested, a preferred ingested amount includes an amount in which a total amount of DHA and EPA of the polyunsaturated fatty acid would be 1 g or more/day, or in the case of a conjugated linoleic acid, the amount used would be from 1 to 4 g/day. In the case where a fat or oil composition is absorbed transdermally, a preferred ingested amount includes an amount in which a total amount of DHA and EPA of the polyunsaturated fatty acid would be 1 g or more/day, or in the case of a conjugated linoleic acid, the amount used would be from 1 to 4 g/day. In addition, the fat or oil composition may be used singly or in multiple times per day within the desired range in the amount used, and the time used and the period are optional.

The subjects using the fat or oil composition of the present invention, in both of Embodiment 1 and Embodiment 2, include human in need of improvement in an action of physiological activity, preferably including an action of lowering blood neutral fats, an action of controlling blood pressure, activation of immune functions, amelioration of allergic symptoms, prevention of dementia, an anti-inflammatory action, improvement in learning functions, an action of lowering body fats, an anti-fatigue action, enhancing action of muscle strength, or suppression of arteriosclerosis. Since the fat or oil composition of the present invention is a safe composition, patients also suffering from another diseases or general normal individuals can be subjects of use, and further the subjects may also be animals such as pets.

As the fat or oil composition of Embodiment 1 of the present invention, for example, one example of an embodiment which is a fat or oil composition containing 80% by weight or more of the fat or oil is shown. It is preferable that the composition contains 80 to 99.999% by weight of a polyunsaturated fatty acid-containing fat or oil, and 0.001 to 20% by weight of a flavor improver, and it is more preferable that the composition contains 90 to 99.9% of a polyunsaturated fatty acid-containing fat or oil, and 0.01 to 10% of a flavor improver. In addition, the remainder components in a case where a total value of the above components does not meet 100% by weight may be properly set with other components according to a known method.

As the fat or oil composition of Embodiment 2 of the present invention, for example, one example of a compositional proportion of an embodiment which is a fat or oil composition containing a fat or oil in an amount of 50% by weight or more is shown. It is preferable that the composition contains 50 to 99.998% by weight of a fat or oil containing a polyunsaturated fatty acid having 18 or more carbon atoms and having two or more double bonds, 0.001 to 10% by weight of a basic amino acid and/or a basic peptide, and 0.001 to 60% by weight of an emulsifying agent, and it is more preferable that the composition contains 50 to 99.98% by weight of a fat or oil containing a polyunsaturated fatty acid having 18 or more carbon atoms and having two or more double bonds, 0.01 to 5% by weight of a basic amino acid and/or a basic peptide, and 0.01 to 50% by weight of an emulsifying agent. In addition, in a case where a total value of the above components does not meet 100% by weight, the remainder components may be properly set with other components according to a known method.

Also, as the fat or oil composition of Embodiment 2 of the present invention, one example of a compositional proportion of an embodiment which is an emulsion composition is shown. It is preferable that the composition contains 1 to 60% by weight of a fat or oil containing a polyunsaturated fatty acid having 18 or more carbon atoms and having two or more double bonds, 0.001 to 10% by weight of a basic amino acid and/or a basic peptide, and 0.001 to 40% by weight of an emulsifying agent, and it is more preferable that the composition contains 5 to 50% by weight of a fat or oil containing a polyunsaturated fatty acid having 18 or more carbon atoms and having two or more double bonds, 0.01 to 5% by weight of a basic amino acid and/or a basic peptide, and 0.01 to 30% by weight of an emulsifying agent, % by weight, and it is even more preferable that the composition contains 10 to 40% by weight of a fat or oil containing a polyunsaturated fatty acid having 18 or more carbon atoms and having two or more double bonds, 0.1 to 3% by weight of a basic amino acid and/or a basic peptide, and 0.1 to 20% by weight of an emulsifying agent, % by weight. In addition, in a case where a total value of the above components does not meet 100% by weight, the remainder components may be properly set with water and/or an alcohol, or other components according to a known method.

Also, as the fat or oil composition of Embodiment 2 of the present invention, one example of a compositional proportion of an embodiment which is a powder composition is shown. It is preferable that the composition contains 1 to 80% by weight of a fat or oil containing a polyunsaturated fatty acid having 18 or more carbon atoms and having two or more double bonds, 0.001 to 20% by weight of a basic amino acid and/or a basic peptide, and 0.001 to 50% by weight of an emulsifying agent, and it is more preferable that the composition contains 5 to 60% by weight of a fat or oil containing a polyunsaturated fatty acid having 18 or more carbon atoms and having two or more double bonds, 0.01 to 10% by weight of a basic amino acid and/or a basic peptide, and 0.01 to 40% by weight of an emulsifying agent, and it is even more preferable that the composition contains 10 to 40% by weight of a fat or oil containing a polyunsaturated fatty acid having 18 or more carbon atoms and having two or more double bonds, 0.1 to 5% by weight of a basic amino acid and/or a basic peptide, and 0.1 to 30% by weight of an emulsifying agent. In addition, in a case where a total value of the above components does not meet 100% by weight, the remainder components may be properly set with other components such as an excipient according to a known method.

The present invention also provides a composition characterized in that the composition contains a fat or oil composition of the present invention. Specific compositions include, for example, an embodiment where a fat or oil composition of Embodiment 1 of the present invention is contained, in other words, an embodiment in which a polyunsaturated fatty acid-containing fat or oil and a basic peptide are blended together, and another embodiment which is an embodiment where a composition containing a fat or oil containing a polyunsaturated fatty acid is blended with a basic peptide. In addition, the compositions include an embodiment where a fat or oil composition of Embodiment 2 of the present invention is contained, in other words, an embodiment in which a polyunsaturated fatty acid-containing fat or oil, a basic amino acid and/or a basic peptide, and an emulsifying agent are blended together, and another embodiment which is an embodiment where a composition containing a fat or oil containing a polyunsaturated fatty acid is blended with a basic amino acid and/or a basic peptide and an emulsifying agent. Further, the compositions include an embodiment in which an emulsion composition of the present invention and/or a powder composition of the present invention is contained. By having the above features, these compositions can be suitably used, for example, as foodstuff, a pharmaceutical composition, or cosmetics.

The foodstuff may be any of those containing a fat or oil composition of the present invention in any of the forms, and include foodstuff for exhibition or improvement for action of physiological activity including an action of lowering blood neutral fats, an action of controlling blood pressure, activation of immune functions, amelioration of allergic symptoms, prevention of dementia, an anti-inflammatory action, improvement in learning functions, an action of lowering body fats, an anti-fatigue action, enhancing action of muscle strength, or suppression of arteriosclerosis. Specifically, it is considered to be possible to provide as foods for specified health use, foods with nutritional functional claims, foods for aged people, foods for special applications, functional foods, health supplements, with an indication that the foods are used, for example, for exhibiting, improving or maintaining the above actions.

The foodstuff include, for example, instant foods such as instant noodles, pot noodles, retort pouched cooked foods, canned foods, microwave-cooking foods, instant soups and stews, and instant miso soups and clear soups, canned soups, and freeze-dried foods; luxury beverages such as carbonated drinks, fresh fruit juices, fruit juice beverages, refreshing beverages (including fruit juices), fruit pulp-containing beverages, fruit grains-containing fruit meat foods, vegetable-based beverages, soya milk and soya milk beverages, coffee beverages, green tea beverages, jelly beverages, powder beverages, concentrated beverages, sports beverages, nutritious beverages, and alcoholic beverages; wheat flour foods such as bread, macaroni, spaghetti, noodles, cake mix, deep frying powder, bread crumbs, and skins of Chinese dumplings or egg rolls; confectionaries such as caramels, candies, chewing gums, chocolates, cookies, biscuits, cakes, pies, snacks, crackers, Japanese confectionaries, rice snacks, bean snacks, baked snacks, jelly, custard pudding, Bavarian cream, and dessert confectionaries; basic seasonings such as soy sauce, miso, sauces, tomato-processed seasonings, sweet rice wine, vinegar, sweeteners, fish sauce extracted from fermented salted fish, and nuoc mam; compound seasonings such as flavor seasonings, culinary mix, roux for curry sauce, mixed sauces, salad dressings, soups for noodles, and spices; fats and oils foods such as butter, margarine, and mayonnaise; milk and dairy products such as milks and processed milks, milk beverages, yogurts, fermented milk beverages, lactobacilli beverages, cheese, ice creams, preparation powder milk, preparation powder milk for infants, and creams; egg processed foods such as liquid eggs, and kinshi-tamago(thinly shredded egg omelet, frozen foods such as semi-cooked frozen foods and cooked frozen foods; processed marine products such as marine canned foods and pastes, hams and sausages made of fish meat, and marine pastes, fishery delicacies, marine dry products, and tsukudani; livestock processed products such as livestock canned foods and pastes, livestock hams and sausages, and livestock delicacies; agricultural processed products such as agricultural canned foods, fruit cans, fruit sauces, fruit preparations, jams and marmalades, pickles, cooked beans, and agricultural dry products, and cereals; nutritious foods such as fluid diet, baby foods, weaning foods, stuff sprinkled over rice, seaweed for ochazuke, and bar foods; supplements, pills, hard capsules, soft capsules, tablets (including raw tablets, sugar-coated tablets, orally fast disintegrating tablets, chewable tablets, foaming tablets, troches, film coating tablets, etc.); and the like. Here, the timing of addition or the method of addition thereof is not particularly limited, so long as these are added to the existing foods, during or after the preparation of the fat or oil composition, the emulsion composition, and/or the powder composition of the present invention.

The pharmaceutical composition can be widely utilized as medicaments and quasi-drugs. For example, the pharmaceutical composition can be used for the treatment or prevention of any disease in want of exhibition or improvement in an action of physiological activity including an action of lowering blood neutral fats, an action of controlling blood pressure, activation of immune functions, amelioration of allergic symptoms, prevention of dementia, an anti-inflammatory action, improvement in learning functions, an action of lowering body fats, an anti-fatigue action, enhancing action of muscle strength, or suppression of arteriosclerosis. Specifically, the pharmaceutical composition can be suitably used in application of treatment or prevention of hyperlipemia, allergic symptoms, arteriosclerosis, and the like. Here, the pharmaceutical composition of the present invention can also be prepared by blending with other components having the same action as the oil or fat composition of the present invention.

The forms of the formulation of the pharmaceutical composition is not particularly limited, so long as the pharmaceutical composition contains an oil or fat composition of the present invention in any of the forms. Specific examples include powders, fine powders, fine granules, granules, pills, capsules, tablets, including raw tablets, sugar-coated tablets, orally fast disintegrating tablets, chewable tablets, foaming tablets, troches, film coating tablets, etc., dry syrups, films, solutions, including suspensions, emulsions, syrups, lemonade, etc., and jelly agents, and may also include confectionary agents such as candies, gummies, and nougat. Here, the capsules include, in addition to hard capsules, soft capsules in which an oil or fat composition or an emulsion composition of the present invention is directly filled.

Cosmetics include cosmetics for exhibition or improvement in physiological activity such as activation of immune functions, amelioration of allergic symptoms, action of promoting blood circulation, an anti-inflammatory action, or an anti-wrinkling action. Specifically, the cosmetics can be suitably used in applications of improvements or prevention of inflammations and wrinkles.

The cosmetics may be any ones so long as an oil or fat composition of the present invention may be contained in any forms, and include lotions, milky lotions, creams, and the like that are purposed for exhibition or improvement in physiological activity such as activation of immune functions, amelioration of allergic symptoms, action of promoting blood circulation, an anti-inflammatory action, or an anti-wrinkling action. In addition, the dosage form is not particularly limited, and can be various externally applicable forms such as solutions, emulsions, creams, gels, ointments, solutions, powders, pastes, cataplasms, plasters, and aerosols.

The foodstuff of the present invention, the pharmaceutical composition of the present invention, and the cosmetics of the present invention can be prepared by blending, in addition to the fat or oil composition of the present invention mentioned above, a carrier, a basal agent, and/or an additive or the like that is ordinarily used in formulation field, food field, and the like in a proper amount within the range that would achieve the object of the present invention. For example, such components include emulsifying agents such as glycerol fatty acid esters, sorbitan fatty acid esters, polyoxyethylene sorbitan fatty acid esters; antioxidants such as tocopherols, catechins, and ascorbic acids; and amino acids such as lysine, arginine, threonine, tryptophan, theanine, and glutamate. Here, the content of the fat or oil composition of the present invention in these foodstuff, pharmaceutical composition, and cosmetics is a suitable amount used of the fat or oil composition of the present invention mentioned above, for example, when orally ingested, the content may be properly by a conventional method set so that a total amount of DHA and EPA of the polyunsaturated fatty acid is 1 g or more/day, or in the case of conjugated linoleic acid, the content is from 1 to 4 g/day. In a case where the fat or oil composition is transdermally absorbed, the content may be properly set according to a conventional method so that a total amount of DHA and EPA of the polyunsaturated fatty acid is 1 g or more/day, or in the case of conjugated linoleic acid, the content is from 1 to 4 g/day. In addition, the foodstuff of the present invention, the pharmaceutical composition of the present invention, and the cosmetics of the present invention may be ingested singly or in multiple times per day within the desired range of the ingested amount, and the time used and the period are optional. For example, in cosmetics, a beverage such as a coffee beverage, a vegetable-based beverage, a fruit juice beverage, a nutritional beverage, or a refreshing drink, a dairy product such as a milk or processed milk, a milk beverage, a fermented milk beverage, a yogurt, custard pudding or jelly, cheese, cream, or ice cream, fruit preparation, an egg granule, or furikake sprinkles, it can be blended so that the content of the polyunsaturated fatty acid is from 0.1 to 4,000 mg/100 g. In addition, in bread, baked confectionary, chocolate, caramel candy, balanced nutritional food such as bar food, snacks such as snack crackers, instant soups, dressings, tablet, capsule, preparation milk for infants, it can be blended so that the content thereof is from 0.1 to 4,000 mg/1 meal.

The fat or oil composition of the present invention exhibits some effects that the generation of unpleasant taste or flavor is suppressed, while containing a polyunsaturated fatty acid. Accordingly, the present invention also provides a method for improving a flavor of a polyunsaturated fatty acid-containing fat or oil, characterized in that a basic peptide is contained in a fat or oil containing a polyunsaturated fatty acid having 18 or more carbon atoms and having two or more double bonds.

The method for improving a flavor of a polyunsaturated fatty acid-containing fat or oil is not particularly limited, so long as the basic peptide is included in a polyunsaturated fatty acid-containing fat or oil in particular.

Here, in the method for improving a flavor of a polyunsaturated fatty acid-containing fat or oil mentioned above, the kinds of the basic peptide used, the content thereof, the content proportion, and the kinds of other components added and blended thereto, the preparation method, the applications, the formulation forms, the ingestion subjects, and the like are the same as in the fat or oil composition of Embodiment 1 of the present invention mentioned above.

In addition, the fat or oil composition of the present invention exhibits some effects that the generation of unpleasant taste and flavor is suppressed while including a polyunsaturated fatty acid. Accordingly, the present invention also provides a method for reducing an off-flavor of a polyunsaturated fatty acid-containing fat or oil, characterized by the inclusion of an emulsifying agent together with a basic amino acid and/or a basic peptide, in a fat or oil containing a polyunsaturated fatty acid having 18 or more carbon atoms and two or more double bonds.

The method for reducing an off-flavor of a polyunsaturated fatty acid-containing fat or oil is not particularly limited, so long as the an emulsifying agent together with a basic amino acid and/or a basic peptide, is included in a fat or oil containing a polyunsaturated fatty acid.

Here, in the method for reducing an off-flavor of a polyunsaturated fatty acid-containing fat or oil mentioned above, the blending of the basic amino acid and/or the basic peptide and the emulsifying agent may be concurrently or separately, and the orders are not particularly limited. In addition, in these methods, the kinds of the basic amino acid and/or the basic peptide and the emulsifying agent used, the content thereof, the content proportion, and the kinds of other components added and blended thereto, the preparation method, the applications, the formulation forms, the ingestion subjects, and the like are the same as in the fat or oil composition of Embodiment 2 of the present invention mentioned above.

EXAMPLES

The present invention will be explained hereinbelow based on Examples, without intending to limit the present invention to these Examples and the like.

Test Example 1-1

Effects of peptides as listed in Table 1 on deodorization and off-flavor suppression of DHA, EPA-containing fish oils were confirmed.

Specifically, to 99 g of a DHA, EPA-containing refined fish oil (manufactured by Maruha Nichiro Foods, DHA content: 22% by weight, EPA content: 5% by weight) was gradually added 1 g of a peptide in fine powder of the kinds as listed in Table 1, while stirring the contents with a homomixer at 3,000 rpm. Thereafter, the mixture was stirred well for 10 minutes, to give a DHA, EPA-containing refined fish oil formulation [polyunsaturated fatty acid/peptide (weight ratio)=26.73/1].

The formulations obtained were divided in three aliquots, and tightly sealed, which were evaluated as follows.
Sample for evaluating initial fish odor: sample that was allowed to stand at 25° C. for 10 minutes,
Sample A for evaluating off-flavor: sample that was allowed to stand at 55° C. for 24 hours, and
Sample B for evaluating off-flavor: sample that was allowed to stand at 37° C. for 3 months.

The fish odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no fish odor was found as 0, and a case where a fish odor was strongly felt as 10. During the evaluation, normalization was carried out so that a score average of the evaluation sample for the initial fish odor of Reference Example 1-1 would be 5.0, and comparisons were made between the samples. The results are shown in Table 1.

TABLE 1

| | | Ref. Ex. | Ex. | | Comp. Ex. | |
|---|---|---|---|---|---|---|
| | | 1-1 | 1-1 | 1-2 | 1-1 | 1-2 |
| DHA, EPA-Containing Fish Oil | | ○ | ○ | ○ | ○ | ○ |
| Basic Peptide | Polylysine | — | ○ | — | — | — |
| | Protamine | — | — | ○ | — | — |
| Acidic Peptide | Polyglutamic acid | — | — | — | ○ | — |
| Neutral Peptide | Glycyl glycine | — | — | — | — | ○ |
| Initial Fish Odor | | 5.0 | 3.6 | 3.5 | 4.8 | 4.6 |
| Off-Flavor A (55° C., 24 h) | | 8.5 | 4.6 | 5.3 | 7.5 | 7.1 |
| Off-Flavor B (37° C., 3 M) | | 8.8 | 5.2 | 5.4 | 8.3 | 7.2 |

It was clarified from Table 1 that the basic peptide effectively suppresses initial fish odor and off-flavor, and the effects lasted over a long time period. On the other hand, in the comparative examples in which an acidic peptide or neutral peptide was added, effects on suppressing initial fish odor and off-flavor were only slightly found, and especially the effects of the acidic peptide did not last.

Test Example 1-2

Effects of peptides as listed in Table 2 on deodorization and off-flavor suppression of the conjugated linoleic acid-containing fats or oils were confirmed.

Specifically, to 99.7 g of a conjugated linoleic acid-containing fat or oil (manufactured by The Nissin OilliO Group, Ltd., conjugated linoleic acid content: 80% by weight) was gradually added 0.3 g of a peptide in fine powder of the kinds as listed in Table 2, while stirring the contents with a homomixer at 3,000 rpm. Thereafter, the mixture was stirred well for 10 minutes, to give a conjugated linoleic acid-containing fat or oil formulation [polyunsaturated fatty acid/peptide (weight ratio)=265.87/1].

The formulations obtained were divided in three aliquots, and tightly sealed, which were evaluated as follows.
Sample for evaluating initial fish odor: sample that was allowed to stand at 25° C. for 10 minutes,
Sample A for evaluating off-flavor: sample that was allowed to stand at 55° C. for one week, and
Sample B for evaluating off-flavor: sample that was allowed to stand at 37° C. for 4 months.

The odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no odor was found as 0, and a case where a odor was strongly felt as 10. During the evaluation, normalization was carried out so that a score average of the evaluation sample for initial odor of Reference Example 1-2 would be 5.0, and comparisons were made between the samples. The results are shown in Table 2.

TABLE 2

| | | Ref. Ex. | Ex. | | Comp. Ex. | |
|---|---|---|---|---|---|---|
| | | 1-2 | 1-3 | 1-4 | 1-3 | 1-4 |
| Conjugated Linoleic Acid-Containing Fat or Oil | | ○ | ○ | ○ | ○ | ○ |
| Basic Peptide | Polylysine | — | ○ | — | — | — |
| | Protamine | — | — | ○ | — | — |
| Acidic Peptide | Polyglutamic acid | — | — | — | ○ | — |
| Neutral Peptide | Glycyl glycine | — | — | — | — | ○ |
| Initial Odor | | 5.0 | 4.1 | 3.8 | 4.8 | 4.6 |
| Off-Flavor A (55° C., 1 W) | | 7.6 | 4.6 | 5.2 | 7.2 | 6.8 |
| Off-Flavor B (37° C., 4 M) | | 7.2 | 4.8 | 4.9 | 7.3 | 6.9 |

It was clarified from Table 2 that the basic peptide effectively suppresses initial odor and off-flavor, and the effects lasted over a long time period. On the other hand, in the comparative examples in which an acidic peptide or neutral peptide was added, effects of suppressing initial odor and off-flavor were only slightly found, and especially the effects of the acidic peptide did not last.

Test Example 1-3

Effects of peptides as listed in Table 3 on deodorization and off-flavor suppression of EPA-containing fish oils were confirmed.

Specifically, to 99.5 g of an EPA-containing refined fish oil (manufactured by NOF Corporation, EPA content: 28% by weight) was gradually added 0.5 g of a peptide in fine powder of the kinds as listed in Table 3, while stirring the contents with a homomixer at 3,000 rpm. Thereafter, the mixture was stirred well for 10 minutes, to give an EPA-containing refined fish oil formulation [polyunsaturated fatty acid/peptide (weight ratio)=55.72/1].

The formulations obtained were divided in three aliquots, and tightly sealed, which were evaluated as follows.
Sample for evaluating initial fish odor: sample that was allowed to stand at 25° C. for 10 minutes,
Sample A for evaluating off-flavor: sample that was allowed to stand at 55° C. for 24 hours, and
Sample B for evaluating off-flavor: sample that was allowed to stand at 37° C. for 3 months.

The fish odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no fish odor was found as 0, and a case where a fish odor was strongly felt as 10. During the evaluation, normalization was carried out so that a score average of the evaluation sample for the initial fish odor of Reference Example 1-3 would be 5.0, and comparisons were made between the samples. The results are shown in Table 3.

TABLE 3

|  |  | Ref. Ex. | Ex. | | Comp. Ex. | |
|---|---|---|---|---|---|---|
|  |  | 1-3 | 1-5 | 1-6 | 1-5 | 1-6 |
| EPA-Containing Fish Oil | | ○ | ○ | ○ | ○ | ○ |
| Basic Peptide | Polylysine | — | ○ | — | — | — |
|  | Protamine | — | — | ○ | — | — |
| Acidic Peptide | Polyglutamic acid | — | — | — | ○ | — |
| Neutral Peptide | Glycyl glycine | — | — | — | — | ○ |
| Initial Fish Odor | | 5.0 | 3.1 | 3.5 | 4.8 | 4.5 |
| Off-Flavor A (55° C., 24 h) | | 8.0 | 4.2 | 4.6 | 7.7 | 6.8 |
| Off-Flavor B (37° C., 3 M) | | 8.5 | 4.8 | 5.1 | 8.2 | 7.1 |

It was clarified from Table 3 that the basic peptide effectively suppresses initial fish odor and off-flavor, and the effects lasted over a long time period. On the other hand, in the comparative examples in which an acidic peptide or neutral peptide was added, effects on suppressing initial fish odor and off-flavor were only slightly found, and especially the effects of the acidic peptide did not last.

Test Example 1-4

Effects of peptides as listed in Table 4 on deodorization and off-flavor suppression of DHA, EPA-containing fish oils were confirmed.

Specifically, to 50 g of a DHA, EPA-containing refined fish oil (manufactured by Maruha Nichiro Foods, DHA content: 19% by weight, EPA content: 3.5% by weight) was gradually added 50 g of a peptide in fine powder of the kinds as listed in Table 4, while stirring the contents with a homogenizer at 6,000 rpm. Thereafter, the mixture was stirred well for 10 minutes, to give a DHA, EPA-containing refined fish oil formulation [polyunsaturated fatty acid/peptide (weight ratio)=0.225/1].

The formulations obtained were divided in three aliquots, and tightly sealed, which were evaluated as follows.
Sample for evaluating initial fish odor: sample that was allowed to stand at 25° C. for 10 minutes,
Sample A for evaluating off-flavor: sample that was allowed to stand at 55° C. for one week, and
Sample B for evaluating off-flavor: sample that was allowed to stand at 37° C. for 6 months.

The fish odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no fish odor was found as 0, and a case where a fish odor was strongly felt as 10. During the evaluation, normalization was carried out so that a score average of the evaluation sample for the initial fish odor of Reference Example 1-4 would be 5.0, and comparisons were made between the samples. The results are shown in Table 4.

TABLE 4

|  |  | Ref. Ex. | Ex. | | Comp. Ex. | |
|---|---|---|---|---|---|---|
|  |  | 1-4 | 1-7 | 1-8 | 1-7 | 1-8 |
| DHA, EPA-Containing Fish Oil | | ○ | ○ | ○ | ○ | ○ |
| Basic Peptide | Polylysine | — | ○ | — | — | — |
|  | Protamine | — | — | ○ | — | — |
| Acidic Peptide | Polyglutamic acid | — | — | — | ○ | — |
| Neutral Peptide | Glycyl glycine | — | — | — | — | ○ |
| Initial Fish Odor | | 5.0 | 2.8 | 3.1 | 4.8 | 4.1 |
| Off-Flavor A (55° C., 1 W) | | 8.7 | 4.6 | 4.5 | 7.0 | 6.6 |
| Off-Flavor B (37° C., 6 M) | | 8.9 | 5.2 | 5.3 | 8.5 | 7.4 |

It was clarified from Table 4 that the basic peptide effectively suppresses initial fish odor and off-flavor, and the effects lasted over a long time period. On the other hand, in the comparative examples in which an acidic peptide or neutral peptide was added, effects on suppressing initial fish odor and off-flavor were only slightly found, and especially the effects of the acidic peptide did not last.

Test Example 1-5

Effects of peptides as listed in Table 5 on deodorization and off-flavor suppression of DHA, EPA-containing fish oils were confirmed.

Specifically, to 99.98 g of a DHA, EPA-containing refined fish oil (manufactured by Maruha Nichiro Foods, DHA content: 38% by weight, EPA content: 4.2% by weight) was gradually added 0.02 g of a peptide in fine powder of the kinds as listed in Table 5, while stirring the contents with a homogenizer at 6,000 rpm. Thereafter, the mixture was stirred well for 10 minutes, to give a DHA, EPA-containing refined fish oil formulation [polyunsaturated fatty acid/peptide (weight ratio)=2109.6/1].

The formulations obtained were divided in three aliquots, and tightly sealed, which were evaluated as follows.
Sample for evaluating initial fish odor: sample that was allowed to stand at 25° C. for 10 minutes,
Sample A for evaluating off-flavor: sample that was allowed to stand at 55° C. for 24 hours, and
Sample B for evaluating off-flavor: sample that was allowed to stand at 37° C. for 1 month.

The fish odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no fish odor was found as 0, and a case where a fish odor was strongly felt as 10. During the evaluation, normalization was carried out so that a score average of the evaluation sample for the initial fish odor of Reference Example 1-5 would be 5.0, and comparisons were made between the samples. The results are shown in Table 5.

TABLE 5

|  |  | Ref. Ex. | Ex. | | Comp. Ex. | |
|---|---|---|---|---|---|---|
|  |  | 1-5 | 1-9 | 1-10 | 1-9 | 1-10 |
| DHA, EPA-Containing Fish Oil | | ○ | ○ | ○ | ○ | ○ |
| Basic Peptide | Polylysine | — | ○ | — | — | — |
|  | Protamine | — | — | ○ | — | — |
| Acidic Peptide | Polyglutamic acid | — | — | — | ○ | — |
| Neutral Peptide | Glycyl glycine | — | — | — | — | ○ |
| Initial Fish Odor | | 5.0 | 3.9 | 4.1 | 5.0 | 4.7 |
| Off-Flavor A (55° C., 24 h) | | 7.6 | 53 | 5.8 | 7.4 | 6.8 |
| Off-Flavor B (37° C., 1 M) | | 8.4 | 5.5 | 5.7 | 7.9 | 7.0 |

It was clarified from Table 5 that the basic peptide effectively suppresses initial fish odor and off-flavor even at a low concentration, and the effects lasted over a long time period. On the other hand, in the comparative examples in which an acidic peptide or neutral peptide was added, effects on suppressing initial fish odor and off-flavor were only slightly found, and especially the effects of the acidic peptide did not last.

Test Example 2-1

Effects of basic amino acids or basic peptides as listed in Table 6 on deodorization and off-flavor suppression of fish oils were confirmed.

Specifically, to 94.9 g of a fish oil (manufactured by Maruha Nichiro Foods, DHA content: 22% by weight, EPA content: 5% by weight) was added 5 g of an emulsifying agent: diglycerol monooleate (manufactured by Taiyo Kagaku Co., Ltd., SUNSOFT Q-17D, HLB=7.0), and sufficiently stirred with a homomixer at 40° C., and 0.1 g of an amino acid or a peptide of the kinds as listed in Table 6 was then gradually added thereto, while stirring the contents with a homomixer at 3,000 rpm. Thereafter, the mixture was stirred well for 10 minutes, to give a DHA, EPA-containing refined fish oil formulation. Here, a weight ratio of the polyunsaturated fatty acid to the amino acid and/or peptide [polyunsaturated fatty acid/(basic amino acid+basic peptide)] was 256/1, and a weight ratio of the polyunsaturated fatty acid to the emulsifying agent [polyunsaturated fatty acid/emulsifying agent] was 5.1/1.

The formulations obtained were divided in three aliquots, and tightly sealed, which were evaluated as follows.

Sample for evaluating initial fish odor: sample that was allowed to stand at 25° C. for 10 minutes, Sample A for evaluating off-flavor: sample that was allowed to stand at 55° C. for 24 hours, and Sample B for evaluating off-flavor: sample that was allowed to stand at 37° C. for 3 months.

The fish odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no fish odor was found as 0, and a case where a fish odor was strongly felt as 10. During the evaluation, normalization was carried out so that a score average of the evaluation sample for the initial fish odor of Reference Example 2-1 would be 5.0, and comparisons were made between the samples. Also, the samples for initial fish odor were evaluated for their external appearances. The results are shown in Table 6.

TABLE 6

|  |  | Ref. Ex. | Comp. Ex. | Ex. | | | Comp. Ex. | | | | | | Ex. | | Comp. Ex. | | | |
|---|---|---|---|---|---|---|---|---|---|---|---|---|---|---|---|---|---|---|
|  |  | 2-1 | 2-1 | 2-1 | 2-2 | 2-3 | 2-2 | 2-3 | 2-4 | 2-5 | 2-6 | 2-7 | 2-4 | 2-5 | 2-8 | 2-9 | 2-10 | 2-11 |
| Fish Oil | | ○ | ○ | ○ | ○ | ○ | ○ | ○ | ○ | ○ | ○ | ○ | ○ | ○ | ○ | ○ | ○ | ○ |
| Emulsifying Agent | | — | ○ | ○ | ○ | ○ | ○ | ○ | ○ | ○ | ○ | ○ | ○ | ○ | — | — | — | — |
| Basic Amino Acid | Arginine | — | — | ○ | — | — | — | — | — | — | — | — | — | — | ○ | — | — | — |
|  | Lysine | — | — | — | ○ | — | — | — | — | — | — | — | — | — | — | — | — | — |
|  | Histidine | — | — | — | — | ○ | — | — | — | — | — | — | — | — | — | — | — | — |
| Neutral Amino Acid | Leucine | — | — | — | — | — | ○ | — | — | — | — | — | — | — | — | — | — | — |
|  | Glycine | — | — | — | — | — | — | ○ | — | — | — | — | — | — | — | — | — | — |
|  | Theanine | — | — | — | — | — | — | — | ○ | — | — | — | — | — | — | ○ | — | — |
|  | Glutamine | — | — | — | — | — | — | — | — | ○ | — | — | — | — | — | — | — | — |
| Acidic Amino Acid | Glutamic Acid | — | — | — | — | — | — | — | — | — | ○ | — | — | — | — | — | ○ | — |
|  | Aspartic Acid | — | — | — | — | — | — | — | — | — | — | ○ | — | — | — | — | — | — |
| Basic Peptide | Polylysine | — | — | — | — | — | — | — | — | — | — | — | ○ | — | — | — | — | ○ |
|  | Protamine | — | — | — | — | — | — | — | — | — | — | — | — | ○ | — | — | — | — |
| Initial Fish Odor | | 5.0 | 4.9 | 2.1 | 2.1 | 2.0 | 3.2 | 3.3 | 3.1 | 3.4 | 3.9 | 3.8 | 2.8 | 2.6 | 2.3 | 4.9 | 5.1 | 2.3 |
| Off-Flavor A (55° C., 24 h) | | 8.2 | 7.9 | 2.4 | 2.7 | 2.1 | 3.7 | 3.4 | 3.0 | 3.6 | 5.1 | 4.9 | 2.4 | 2.8 | 6.8 | 6.6 | 7.5 | 6.6 |
| Off-Flavor B (37° C., 3 M) | | 8.8 | 8.5 | 2.1 | 2.4 | 2.3 | 3.9 | 3.4 | 3.3 | 3.7 | 5.0 | 5.2 | 2.6 | 2.5 | 7.1 | 7.3 | 7.4 | 7.1 |
| State (External Appearance) | | T | T | WD | WD | WD | WD | WD | WD | WD | WD | WD | WD | WD | S | S | S | S |

T: transparent
WD: white turbid dispersion
S: separated

It can be seen from Table 6 that the evaluations of the basic amino acid and the basic peptide are excellent, followed by neutral amino acid and acidic amino acid, in that order. It was clarified therefrom that the basic amino acid and the basic peptide effectively suppressed initial fish odor and off-flavor, and the effects lasted over a long time period. On the other hand, in Comparative Example 2-1 where an amino acid was not added, effects for reducing initial fish odor and off-flavor were not found. In addition, in Comparative Examples 2-8 to 2-11 without adding an emulsifying agent, effects on fish odor were low as compared to those of Examples, while showing slight suppression, and the effects did not last, so that the amino acid undesirably precipitated and separated in a very short time, so that it was found that these comparative examples could not establish a manufactured article.

Test Example 2-2

Effects of fish oils of basic amino acids or basic peptides as listed in Table 7 on deodorization and off-flavor suppression were confirmed.

Specifically, 60 g of an emulsifying agent: decaglycerol monostearate (manufactured by Taiyo Kagaku Co., Ltd., SUNSOFT Q-18Y, HLB=17.5) was added to 400 g of glycerol, and sufficient stirred with a homomixer at 70° C., and the temperature of the mixture product was then cooled to 50° C. Thereto 300 g of a refined fish oil (manufactured by NOF Corporation, DHA content: 24% by weight, EPA content: 4% by weight) to which 5 g of an emulsifying agent: decaglycerol tetraoleate (manufactured by Taiyo Kagaku Co., Ltd., SUNSOFT Q-1755, HLB=4.5) was separately added to dissolve to provide a clear solution was then gradually added thereto, while stirring the contents with a homomixer at 3,000 rpm. Next, 230 g of water to which 5 g of an amino acid or a peptide of the kinds as listed in Table 7 was added was gradually supplied thereto while stirring the contents with a homomixer at 3,000 rpm (a part being not completely dissolved but in a dispersion state), and the mixture was then stirred for 10 minutes with a homomixer at 8,000 rpm, to give a DHA, EPA-containing refined fish oil emulsion formulation. Also, a formulation in which an antioxidant was blended was prepared in the same manner as above except that 1 g of tocopherol (manufactured by TAMA BIOCHEMICAL CO., LTD., E-MIX-D) was dissolved together with the emulsifying agent: decaglycerol tetraoleate in the refined fish oil, and that 5 g of a tea extract (manufactured by Taiyo Kagaku Co., Ltd., SUNPHENONE EGCg) and 1 g of ascorbic acid (manufactured by Tanabe Seiyaku Co., Ltd., L-ascorbic acid) were added to an aqueous solution prepared by adding an amino acid or a peptide. Here, as to the formulations not containing an emulsifying agent, an amino acid, a peptide, or an antioxidant, water was added to fill up the volume reduced by the absence thereof to match the total volume. Here, a weight ratio of the polyunsaturated fatty acid to the amino acid and/or peptide [polyunsaturated fatty acid/(basic amino acid+basic peptide)] was 16.8/1, a weight ratio of the polyunsaturated fatty acid to the emulsifying agent [polyunsaturated fatty acid/emulsifying agent] was 1.3/1, and a weight ratio of the polyunsaturated fatty acid to the emulsifying agent having an HLB value of less than 10 [polyunsaturated fatty acid/emulsifying agent] was 16.8/1.

The emulsion formulations obtained were divided in three aliquots, and the samples were stored in the same manner as in Test Example 2-1, and subjected to sensory evaluation. Specifically, a 1% by weight aqueous solution of the samples obtained was directly ingested, and the level of senses felt by the panelists was scored, and a score average of 10 panelists was calculated by defining a case where no fish odor was found as 0, and a case where a fish odor was strongly felt as 10. Also, the initial fish odor samples were evaluated for their external appearances. As normalization of a score, the normalization was carried out so that a score average of the initial fish odor of Reference Example 2-2 would be 5.0, and comparisons were made between the samples. The results are shown in Table 7.

TABLE 7

| | | Ref. Ex. 2-2 | Comp. Ex. 2-12 | Ex. | | | Comp. Ex. | | | | | |
|---|---|---|---|---|---|---|---|---|---|---|---|---|
| | | | | 2-6 | 2-7 | 2-8 | 2-13 | 2-14 | 2-15 | 2-16 | 2-17 | 2-18 |
| | Fish Oil | ○ | ○ | ○ | ○ | ○ | ○ | ○ | ○ | ○ | ○ | ○ |
| | Water | ○ | ○ | ○ | ○ | ○ | ○ | ○ | ○ | ○ | ○ | ○ |
| | Glycerol | ○ | ○ | ○ | ○ | ○ | ○ | ○ | ○ | ○ | ○ | ○ |
| | Emulsifying Agent | — | ○ | ○ | ○ | ○ | ○ | ○ | ○ | ○ | ○ | ○ |
| Basic Amino Acid | Arginine | — | — | ○ | — | — | — | — | — | — | — | — |
| | Lysine | — | — | — | ○ | — | — | — | — | — | — | — |
| | Histidine | — | — | — | — | ○ | — | — | — | — | — | — |
| Neutral Amino Acid | Leucine | — | — | — | — | — | ○ | — | — | — | — | — |
| | Glycine | — | — | — | — | — | — | ○ | — | — | — | — |
| | Theanine | — | — | — | — | — | — | — | ○ | — | — | — |
| | Glutamine | — | — | — | — | — | — | — | — | ○ | — | — |
| Acidic Amino Acid | Glutamic Acid | — | — | — | — | — | — | — | — | — | ○ | — |
| | Aspartic Acid | — | — | — | — | — | — | — | — | — | — | ○ |
| Basic Peptide | Polylysine | — | — | — | — | — | — | — | — | — | — | — |
| | Protamine | — | — | — | — | — | — | — | — | — | — | — |
| | Anitoxidant | — | — | — | — | — | — | — | — | — | — | — |
| | Initial Fish Odor | 5.0 | 4.9 | 0.4 | 0.3 | 0.4 | 1.2 | 1.4 | 1.3 | 1.6 | 4.1 | 4.0 |
| | Off-Flavor A (55° C., 24 h) | 9.4 | 9.5 | 0.3 | 0.3 | 0.4 | 1.5 | 1.6 | 1.5 | 1.8 | 4.3 | 4.4 |
| | Off-Flavor B (37° C., 3 M) | 9.6 | 9.7 | 0.4 | 0.4 | 0.6 | 1.7 | 1.8 | 1.6 | 1.9 | 4.3 | 4.7 |
| | State (External Appearance) | S | WD | WD | WD | WD | WD | WD | WD | WD | WD | WD |

| | | Ex. | | Comp. Ex. | | | | | Ex. |
|---|---|---|---|---|---|---|---|---|---|
| | | 2-9 | 2-10 | 2-19 | 2-20 | 2-21 | 2-22 | 2-23 | 2-11 |
| | Fish Oil | ○ | ○ | ○ | ○ | ○ | ○ | ○ | ○ |
| | Water | ○ | ○ | ○ | ○ | ○ | ○ | ○ | ○ |
| | Glycerol | ○ | ○ | ○ | ○ | ○ | ○ | ○ | ○ |

TABLE 7-continued

|  |  |  |  |  |  |  |  |  |  |
|---|---|---|---|---|---|---|---|---|---|
| | Emulsifying Agent | ○ | ○ | — | — | — | — | ○ | ○ |
| Basic Amino Acid | Arginine | — | — | ○ | — | — | — | — | — |
| | Lysine | — | — | — | — | — | — | — | — |
| | Histidine | — | — | — | — | — | — | — | ○ |
| Neutral Amino Acid | Leucine | — | — | — | — | — | — | — | — |
| | Glycine | — | — | — | — | — | — | — | — |
| | Theanine | — | — | — | ○ | — | — | — | — |
| | Glutamine | — | — | — | — | — | — | — | — |
| Acidic Amino Acid | Glutamic Acid | — | — | — | — | ○ | — | — | — |
| | Aspartic Acid | — | — | — | — | — | — | — | — |
| Basic Peptide | Polylysine | ○ | — | — | — | — | ○ | — | — |
| | Protamine | — | ○ | — | — | — | — | — | — |
| | Anitoxidant | — | — | — | — | — | — | ○ | ○ |
| | Initial Fish Odor | 0.4 | 0.3 | 1.0 | 4.5 | 4.5 | 1.1 | 4.7 | 0.2 |
| | Off-Flavor A (55° C., 24 h) | 0.3 | 0.3 | 5.8 | 6.2 | 7.3 | 5.9 | 5.7 | 0.3 |
| | Off-Flavor B (37° C., 3 M) | 0.4 | 0.6 | 6.4 | 6.6 | 7.6 | 6.3 | 5.9 | 0.2 |
| | State (External Appearance) | WD | WD | S | S | S | S | WD | WD |

S: separated
WD: white turbid dispersion

It can be seen from Table 7 that the evaluations of the basic amino acid and the basic peptide are excellent, followed by neutral amino acid and acidic amino acid, in that order, in the same manner as in Test Example 2-1. It was clarified therefrom that the basic amino acid and the basic peptide more notably suppressed initial fish odor and off-flavor, and the effects lasted over a long time period, even in the emulsion formulations. On the other hand, in Comparative Example 2-12 where an amino acid was not added, effects for reducing initial fish odor and off-flavor were not found. In addition, in Comparative Examples 2-19 to 2-22 without adding an emulsifying agent, effects on fish odor were low as compared to those of Examples, while showing slight suppression, and the effects did not last, so that they were undesirably separated in a very short time, so that it was found that these comparative examples could not establish a manufactured article. In the system to which an antioxidant was added, Comparative Example 2-23 where the basic amino acid was not added could confirm some but insufficient effects on suppressing off-flavor, and on the other hand, Example 2-11 where the antioxidant and the basic amine were added can be seen to have effects in reducing both initial fish odor and off-flavor. Here, those indicated as "WD (white turbid dispersion)" in the list of results, were excellently dispersed even after the termination of being allowing to stand.

Test Example 2-3

The effects on suppressing off-flavor of beverages prepared by using the emulsion formulations prepared in Test Example 2-2 were confirmed.

Specifically, 2 g of an emulsion formulation prepared in Test Example 2-2 was added to 198 g of water, and the mixture was homogeneously stirred. Thereafter, having confirmed of the sufficient stirring, the mixture was divided in two aliquots, and filled in a soda bottle and sealed with a crown cap. The contents were subjected to retort sterilization at 121° C. for 1 minute, to prepare a beverage sample.

The beverage samples obtained were evaluated as follows:
Sample A for the sample that was allowed to stand at 55° C. for one month, and
Sample B for the sample that was allowed to stand at 37° C. for four months. Each of the samples after storage was subjected to sensory evaluation for flavor. Specifically, as a score of the degree of senses felt by the panelists, a score average of 10 panelists was calculated by defining a case where no fish odor was found as 0, and a case where a fish odor was strongly felt as 10, upon ingestion. Here, as normalization of the score, the normalization was carried out so that a score average of each of Off-Flavors A and B of Comparative Example 2-24 would be 10, and comparisons were made between the samples. The results are shown in Table 8.

TABLE 8

| | | Comp. Ex. | Ex. | | | Comp. Ex. | | | | | | Ex. | | Comp. Ex. | Ex. |
|---|---|---|---|---|---|---|---|---|---|---|---|---|---|---|---|
| | | 2-24 | 2-12 | 2-13 | 2-14 | 2-25 | 2-26 | 2-27 | 2-28 | 2-29 | 2-30 | 2-15 | 2-16 | 2-31 | 2-17 |
| | Fish Oil | ○ | ○ | ○ | ○ | ○ | ○ | ○ | ○ | ○ | ○ | ○ | ○ | ○ | ○ |
| | Water | ○ | ○ | ○ | ○ | ○ | ○ | ○ | ○ | ○ | ○ | ○ | ○ | ○ | ○ |
| | Glycerol | ○ | ○ | ○ | ○ | ○ | ○ | ○ | ○ | ○ | ○ | ○ | ○ | ○ | ○ |
| | Emulsifying Agent | ○ | ○ | ○ | ○ | ○ | ○ | ○ | ○ | ○ | ○ | ○ | ○ | ○ | ○ |
| Basic Amino Acid | Arginine | — | ○ | — | — | — | — | — | — | — | — | — | — | — | — |
| | Lysine | — | — | ○ | — | — | — | — | — | — | — | — | — | — | — |
| | Histidine | — | — | — | ○ | — | — | — | — | — | — | — | — | — | ○ |
| Neutral Amino Acid | Leucine | — | — | — | — | ○ | — | — | — | — | — | — | — | — | — |
| | Glycine | — | — | — | — | — | ○ | — | — | — | — | — | — | — | — |
| | Theanine | — | — | — | — | — | — | ○ | — | — | — | — | — | — | — |
| | Glutamine | — | — | — | — | — | — | — | ○ | — | — | — | — | — | — |
| Acidic Amino Acid | Glutamic Acid | — | — | — | — | — | — | — | — | ○ | — | — | — | — | — |
| | Aspartic Acid | — | — | — | — | — | — | — | — | — | ○ | — | — | — | — |

TABLE 8-continued

|  |  | Comp. Ex. | Ex. | | | Comp. Ex. | | | | | | Ex. | | Comp. Ex. | Ex. |
| --- | --- | --- | --- | --- | --- | --- | --- | --- | --- | --- | --- | --- | --- | --- | --- |
|  |  | 2-24 | 2-12 | 2-13 | 2-14 | 2-25 | 2-26 | 2-27 | 2-28 | 2-29 | 2-30 | 2-15 | 2-16 | 2-31 | 2-17 |
| Basic Peptide | Polylysine | — | — | — | — | — | — | — | — | — | — | ○ | — | — | — |
|  | Protamine | — | — | — | — | — | — | — | — | — | — | — | ○ | — | — |
| Antioxidant |  | — | — | — | — | — | — | — | — | — | — | — | — | ○ | ○ |
| Off-Flavor A (55° C., 1 M) |  | 10 | 0.5 | 0.7 | 0.4 | 3.1 | 3.3 | 3.1 | 3.0 | 6.5 | 6.4 | 0.8 | 1.1 | 8.4 | 0.4 |
| Off-Flavor B (37° C., 4 M) |  | 10 | 0.4 | 0.3 | 0.5 | 2.8 | 3.4 | 3.2 | 2.9 | 6.0 | 6.3 | 0.7 | 0.8 | 8.2 | 0.4 |

It could be seen from Table 8 that the evaluations of the basic amino acid and the basic peptide were excellent, followed by neutral amino acid and acidic amino acid, in that order, in the same manner as in Test Example 2-1. It was clarified therefrom that the basic amino acid and the basic peptide effectively suppressed off-flavor of fish oil over a long time period, even in beverage to which the emulsion formulations were added, whereby suggesting a possibility that DHA, EPA-containing refined fat or oil could be blended in beverages that are stored and distributed at ambient temperatures. On the other hand, in Comparative Example 2-24 where an amino acid was not added, effects for reducing off-flavor were not found. In addition, as to the system in which an antioxidant was added, Comparative Example 2-31 without adding a basic amino acid is shown to have some but insufficient effects on suppressing off-flavor as compared to Comparative Example 2-24, and on the other hand, Example 2-17 where the antioxidant and the basic amine were added can be seen to have effects on reducing off-flavor. Here, since in the systems to which an emulsifying agent was not added (Comparative Examples 2-19 to 2-22 in Test Example 2-2), beverage samples could not be prepared, tests were not conducted thereon.

Test Example 2-4

A fish oil-containing powder formulation was prepared, and the effects on deodorization of fish oil and suppression of off-flavor were confirmed.

Specifically, 60 g of an emulsifying agent: pentaglycerol monomyristate (manufactured by Taiyo Kagaku Co., Ltd., SUNSOFT A-141E, HLB=12.2) was added to 680 g of water, the mixture was sufficiently stirred with a homomixer at 70° C., and the temperature of the mixture product was then cooled to 50° C. A dispersion of 5 g of an amino acid or a peptide as listed in Table 9 in 250 g of a refined fish oil (manufactured by NOF Corporation, DHA content: 24% by weight, EPA content: 4% by weight) which was made into a clear solution by separately dissolving 5 g of an emulsifying agent: glycerol monostearate (manufactured by Taiyo Kagaku Co., Ltd., SUNSOFT No. 8000V, HLB=4.1) thereto was obtained. The dispersion was gradually added to an aqueous phase of the mixture, while stirring the contents with a homomixer at 3,000 rpm, and the mixture was then stirred with a homomixer at 8,000 rpm for 10 minutes, to give an emulsion formulation sample. Here, as to the formulations not containing an emulsifying agent, an amino acid, or a peptide, the portion of reduced volume by the absence of blending was filled up with water to match the total volume. Here, a weight ratio of the polyunsaturated fatty acid to the amino acid and/or peptide [polyunsaturated fatty acid/(basic amino acid+basic peptide)] was 14/1, a weight ratio of the polyunsaturated fatty acid to the emulsifying agent [polyunsaturated fatty acid/emulsifying agent] was 1.1/1, and a weight ratio of the polyunsaturated fatty acid to the emulsifying agent having an HLB value of less than 10 [polyunsaturated fatty acid/emulsifying agent] was 14/1.

Next, 600 g of α-cyclodextrin (manufactured by ENSUIKO SUGAR REFINING CO., LTD., Dexypearl α-100), an excipient, was dissolved in 1,400 g of water, and this solution was mixed with the previously prepared emulsion formulation sample, and thereafter subjected to lyophilization treatment, to give a DHA, EPA-containing refined fish oil powder formulation.

The powder formulation samples obtained were divided in three aliquots and tightly sealed, which were evaluated as follows.

Sample for evaluating initial fish odor: sample that was allowed to stand at 25° C. for 10 minutes, Sample A for evaluating off-flavor: sample that was allowed to stand at 55° C. for 24 hours, and Sample B for evaluating off-flavor: sample that was allowed to stand at 37° C. for 3 months.

Each of the samples after storage was prepared into a 2% by weight aqueous solution respectively, and then ingested. As a score of the degree of senses felt by the panelists, a score average of 10 panelists was calculated by defining a case where no fish odor was found as 0, and a case where a fish odor was strongly felt as 10, upon ingestion. During the evaluation, normalization was carried out so that a score average of the initial fish odor of Reference Example 2-3 would be 5.0, and comparisons in flavor were made between the samples. The external appearances of the aqueous solutions of the initial fish odor samples were also evaluated. The results are shown in Table 9.

TABLE 9

|  |  | Ref. Ex. | Comp. Ex. | Ex. | | Comp. Ex. | | | | Ex. | | Comp. Ex. | | | |
| --- | --- | --- | --- | --- | --- | --- | --- | --- | --- | --- | --- | --- | --- | --- | --- |
|  |  | 2-3 | 2-32 | 2-18 | 2-19 | 2-33 | 2-34 | 2-35 | 2-36 | 2-20 | 2-21 | 2-37 | 2-38 | 2-39 | 2-40 |
|  | Fish Oil | ○ | ○ | ○ | ○ | ○ | ○ | ○ | ○ | ○ | ○ | ○ | ○ | ○ | ○ |
|  | Emulsifying Agent | — | ○ | ○ | ○ | ○ | ○ | ○ | ○ | ○ | ○ | — | — | — | — |
| Basic Amino | Arginine | — | — | ○ | — | — | — | — | — | ○ | — | ○ | — | — | — |
|  | Histidine | — | — | — | ○ | — | — | — | — | — | — | — | — | — | — |

TABLE 9-continued

| | | Ref. Ex. | Comp. Ex. | Ex. | | Comp. Ex. | | | | Ex. | | Comp. Ex. | | | |
|---|---|---|---|---|---|---|---|---|---|---|---|---|---|---|---|
| | | 2-3 | 2-32 | 2-18 | 2-19 | 2-33 | 2-34 | 2-35 | 2-36 | 2-20 | 2-21 | 2-37 | 2-38 | 2-39 | 2-40 |
| Neutral Amino Acid | Glycine | — | — | — | — | ○ | — | — | — | — | — | — | — | — | — |
| | Theanine | — | — | — | — | — | ○ | — | — | — | — | — | ○ | — | — |
| Acidic Amino Acid | Glutamic Acid | — | — | — | — | — | — | ○ | — | — | — | — | — | ○ | — |
| | Aspartic Acid | — | — | — | — | — | — | — | ○ | — | — | — | — | — | — |
| Basic Peptide | Polylysine | — | — | — | — | — | — | — | — | ○ | — | — | — | — | ○ |
| | Protamine | — | — | — | — | — | — | — | — | — | ○ | — | — | — | — |
| Initial Fish Odor | | 5.0 | 5.3 | 0.4 | 0.3 | 1.2 | 1.3 | 3.6 | 3.8 | 0.6 | 0.7 | 1.1 | 4.4 | 4.4 | 1.1 |
| Off-Flavor A (55° C., 24 h) | | 9.2 | 9.3 | 0.2 | 0.5 | 2.6 | 2.8 | 4.9 | 4.7 | 0.4 | 0.6 | 6.6 | 7.1 | 8.2 | 6.9 |
| Off-Flavor B (37° C., 3 M) | | 9.4 | 9.5 | 0.4 | 0.5 | 2.7 | 2.5 | 4.8 | 5.3 | 0.4 | 0.5 | 6.8 | 7.5 | 8.0 | 6.9 |
| State (External Appearance) | | S | WD | WD | WD | WD | WD | WD | WD | WD | WD | S | S | S | S |

S: separated,
WD: white turbid dispersion

It could be seen from Table 9 that the evaluations of the basic amino acid and the basic peptide are excellent, followed by neutral amino acid and acidic amino acid, in that order, in the same manner as in Test Example 2-1. It was clarified therefrom that the basic amino acid and the basic peptide effectively suppressed initial fish odor and off-flavor, and the effects lasted over a long time period, even in the powder formulations. In addition, it could be seen that the composition obtained which was once emulsified was powdered, so that solubility of the amino acid or peptide added was improved, thereby improving the reactivity with bad odor components, whereby the effects are more strongly exhibited. On the other hand, in Comparative Example 2-32 where an amino acid was not added, effects for reducing initial fish odor and off-flavor were not found, and in Comparative Examples 2-37 to 2-40 without adding an emulsifying agent, while initial fish odor and off-flavor are slightly suppressed, they were undesirably separated in a very short time, so that it could be seen that these comparative examples could not be established as a manufactured article.

Test Example 2-5

Effects of basic amino acids or basic peptides as listed in Table 10 on off-flavor suppression of the conjugated linoleic acid-containing fats or oils were confirmed.

Specifically, 60 g of an emulsifying agent: decaglycerol monomyristate (manufactured by Taiyo Kagaku Co., Ltd., SUNSOFT Q-14S, HLB=14.5) was added to 633 g of a reduced starch saccharidization product (manufactured by Mitsubishi Shoji Foodtech Co., Ltd., amameal), and sufficiently stirred with a homomixer at 60° C., and the temperature of the mixture product was then cooled to 50° C. Thereto was gradually supplied a dispersion prepared by previously dispersing 2 g of an amino acid or a peptide of the kinds as listed in Table 10 in 300 g of a conjugated linoleic acid-containing fat or oil (manufactured by The Nissin OilliO Group, Ltd., conjugated linoleic acid content: 80% by weight) in which 5 g of an emulsifying agent: tetraglycerol trimyristate (manufactured by Taiyo Kagaku Co., Ltd., SUNSOFT A-143E, HLB=7.6) was separately dissolved to provide a clear solution, while stirring with a homomixer at 3,000 rpm, and thereafter stirred with a homomixer at 8,000 rpm for 3 minutes. Thereafter, the mixture was treated at a pressure of 245 MPa with a Wet type Atomization Unit (manufactured by SUGINO MACHINE LIMITED, Star Burst), to give a conjugated linoleic acid-containing fat or oil emulsion formulation. Here, as to the formulations not containing an emulsifying agent, an amino acid, or a peptide, the portion of reduced volume by the absence of blending was filled up with the reduced starch saccharidization product to match the total volume. Here, a weight ratio of the polyunsaturated fatty acid to the amino acid and/or peptide [polyunsaturated fatty acid/(basic amino acid+basic peptide)] was 120/1, a weight ratio of the polyunsaturated fatty acid to the emulsifying agent [polyunsaturated fatty acid/emulsifying agent] was 3.7/1, and a weight ratio of the polyunsaturated fatty acid to the emulsifying agent having an HLB value of less than 10 [polyunsaturated fatty acid/emulsifying agent] was 48/1.

The emulsion formulations obtained were divided into two aliquots, and tightly sealed, and sensory evaluation was carried out as follows:

Sample A for evaluating off-flavor: sample that was allowed to stand at 55° C. for one week, and Sample B for evaluating off-flavor: sample that was allowed to stand at 37° C. for four months.

Specifically, a 1% by weight aqueous solution of the stored sample was directly ingested, and as a score of the degree of senses felt by the panelists, a score average of 10 panelists was calculated by defining a case where no off-flavor was found as 0, and a case where an off-flavor was strongly felt as 10. In addition, as to Sample A for evaluating off-flavor, its external appearance was evaluated. Here, as normalization of the score, the normalization was carried out so that a score average of Off-Flavors A and B of Reference Example 2-4 would be 10, and comparisons were made between the samples. The results are shown in Table 10.

TABLE 10

| | Ref. Ex. | Comp. Ex. | Ex. | | | Comp. Ex. | | | | Ex. | | Comp. Ex. | | | |
|---|---|---|---|---|---|---|---|---|---|---|---|---|---|---|---|
| | 2-4 | 2-41 | 2-22 | 2-23 | 2-24 | 2-42 | 2-43 | 2-44 | 2-45 | 2-25 | 2-26 | 2-46 | 2-47 | 2-48 | 2-49 |
| Conjugated Linoleic Acid-Containing Fat or Oil | ○ | ○ | ○ | ○ | ○ | ○ | ○ | ○ | ○ | ○ | ○ | ○ | ○ | ○ | ○ |
| Water | ○ | ○ | ○ | ○ | ○ | ○ | ○ | ○ | ○ | ○ | ○ | ○ | ○ | ○ | ○ |
| Glycerol | ○ | ○ | ○ | ○ | ○ | ○ | ○ | ○ | ○ | ○ | ○ | ○ | ○ | ○ | ○ |
| Emulsifying Agent | — | ○ | ○ | ○ | ○ | ○ | ○ | ○ | ○ | ○ | ○ | — | — | — | — |
| Basic Amino Acid — Arginine | — | — | ○ | — | — | — | — | — | — | — | — | ○ | — | — | — |
| Lysine | — | — | — | ○ | — | — | — | — | — | — | — | — | — | — | — |
| Histidine | — | — | — | — | ○ | — | — | — | — | — | — | — | — | — | — |
| Neutral Amino Acid — Glycine | — | — | — | — | — | ○ | — | — | — | — | — | — | — | — | — |
| Theanine | — | — | — | — | — | — | ○ | — | — | — | — | — | ○ | — | — |
| Acidic Amino Acid — Glutamic Acid | — | — | — | — | — | — | — | ○ | — | — | — | — | — | ○ | — |
| Aspartic Acid | — | — | — | — | — | — | — | — | ○ | — | — | — | — | — | — |
| Basic Peptide — Polylysine | — | — | — | — | — | — | — | — | — | ○ | — | — | — | — | ○ |
| Protamine | — | — | — | — | — | — | — | — | — | — | ○ | — | — | — | — |
| Off-Flavor A (55° C., 1 w) | 10 | 10 | 0.7 | 0.5 | 0.7 | 1.9 | 2.7 | 5.0 | 5.1 | 0.6 | 0.5 | 6.5 | 7.4 | 8.5 | 6.8 |
| Off-Flavor B (37° C., 4 M) | 10 | 10 | 0.6 | 0.7 | 0.7 | 2.1 | 2.4 | 5.5 | 5.4 | 0.5 | 0.7 | 7.6 | 8.3 | 8.8 | 7.5 |
| State (External Appearance) | S | WD | WD | WD | WD | WD | WD | WD | WD | WD | WD | S | S | S | S |

WD: white turbid dispersion
S: separated

It could be seen from Table 10 that the evaluations of the basic amino acid and the basic peptide were excellent, followed by neutral amino acid and acidic amino acid, in that order, in the same manner as in Test Examples 2-1 to 2-4. It was clarified therefrom that the basic amino acid and the basic peptide more remarkably suppressed off-flavor, and the effects lasted over a long time period, even in the emulsion formulations of the fat or oil containing different polyunsaturated fatty acids. On the other hand, in Comparative Example 2-41 where an amino acid was not added, effects for reducing off-flavor were not found, and in Comparative Examples 2-46 to 2-49 without adding an emulsifying agent, while showing slight suppression of an increase in off-flavor, they were undesirably separated in a very short time, so that it was found that these comparative examples could not establish a manufactured article. Here, those indicated as "WD (white turbid dispersion)" in the list of results, were excellently dispersed even after the termination of being allowing to stand.

Test Example 2-6

Effects of basic amino acids on deodorization and off-flavor suppression of refined oils derived from fine algae in cases where an emulsifying agent as listed in Table 11 was blended were confirmed.

Specifically, 5 g of an emulsifying agent as listed in Table 11 was added to 94.5 g of a refined oil derived from fine algae (manufactured by DSM Nutrition, Japan, DHA content: 24% by weight), and sufficiently stirred at 40° C. with a homomixer, and a 0.5 g lysine hydrochloride powder was then gradually added hereto, while stirring with a homomixer at 3,000 rpm, and the mixture was stirred for 10 minutes, to give a DHA-containing refined oil formulation. Here, a weight ratio of the polyunsaturated fatty acid to the amino acid and/or peptide [polyunsaturated fatty acid/(basic amino acid+basic peptide)] was 45/1, and a weight ratio of the polyunsaturated fatty acid to the emulsifying agent [polyunsaturated fatty acid/emulsifying agent] was 4.5/1.

The formulations obtained were divided in three aliquots, and tightly sealed, which were evaluated as follows.
Sample for evaluating initial fish-like odor: sample that was allowed to stand at 25° C. for 10 minutes,
Sample A for evaluating off-flavor: sample that was allowed to stand at 55° C. for 24 hours, and
Sample B for evaluating off-flavor: sample that was allowed to stand at 37° C. for 2 months.

The fish-like odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no fish-like odor was found as 0, and a case where a fish-like odor was strongly felt as 10. Here, as normalization of the score, the normalization was carried out so that a score average of the initial fish-like odor of Reference Example 2-5 would be 5.0, and comparisons were made between the samples. In addition, Sample B for evaluating off-flavor was visually confirmed for its external appearance and the amount of precipitations. The judgment was made by defining Reference Example 5 where no amount of precipitates was found as "0," and defining Comparative Example 50 where the precipitated amount in which all the amino acids were precipitated as "4." The results are shown in Table 11.

TABLE 11

| | Ref. Ex. | Comp. Ex. | Ex. | | | | | |
|---|---|---|---|---|---|---|---|---|
| | 2-5 | 2-50 | 2-27 | 2-28 | 2-29 | 2-30 | 2-31 | 2-32 |
| Refined Oil Derived from Fine Algae | ○ | ○ | ○ | ○ | ○ | ○ | ○ | ○ |
| Lysine Hydrochloride | — | ○ | ○ | ○ | ○ | ○ | ○ | ○ |

TABLE 11-continued

|  |  | Ref. Ex. 2-5 | Comp. Ex. 2-50 | Ex. 2-27 | Ex. 2-28 | Ex. 2-29 | Ex. 2-30 | Ex. 2-31 | Ex. 2-32 |
|---|---|---|---|---|---|---|---|---|---|
| Emulsifying Agent | Q-173Y | — | — | ○ | — | — | — | — | — |
|  | Q-175S | — | — | — | ○ | — | — | — | — |
|  | 8070V | — | — | — | — | ○ | — | — | — |
|  | S-770 | — | — | — | — | — | ○ | — | — |
|  | PL-100 | — | — | — | — | — | — | ○ | — |
|  | SLP-White | — | — | — | — | — | — | — | ○ |
| Initial Fish-Like Odor |  | 5.0 | 4.8 | 2.0 | 2.3 | 2.6 | 2.8 | 2.6 | 2.5 |
| Off-Flavor A (55° C., 24 h) |  | 8.1 | 8.0 | 2.2 | 2.7 | 2.9 | 3.4 | 3.2 | 2.9 |
| Off-Flavor B (37° C., 2 M) |  | 8.0 | 7.8 | 2.1 | 3.0 | 3.4 | 3.9 | 3.8 | 3.7 |
| Sample B | External Appearance | T | T | WD | WD | WD | WD | WD | WD |
|  | Amount of Precipitation | 0 | 4 | 2 | 2 | 2 | 3 | 3 | 3 |

T: transparent,
WD: white turbid dispersion
Q-173Y: Decaglycerol trioleate, manufactured by Taiyo Kagaku Co., Ltd, SUNSOFT Q-173Y, FMB = about 9, primary hydroxyl groups of the polyglycerol: 60.5% by number, hydroxyl value: 810
Q-175S: Decaglycerol trioleate, manufactured by Taiyo Kagaku Co., Ltd, SUNSOFT Q-175S, HLB = 4.5, primary hydroxyl groups of the polyglycerol: 46.9% by number, hydroxyl value: 950
8070V: Glycerol monooleate, manufactured by Taiyo Kagaku Co., Ltd, SUNSOFT No. 8070V, HLB = 4.1
S-770: Sucrose stearate, manufactured by Mitsubishi-Kagaku Foods Corporation, RYOTO Sugar Ester S-770, HLB = about 7
PL-100: Propylene glycol monolaurate, manufactured by RIKEN VITAMIN CO., LTD. RIKEMAL PL-100, HLB = 4.2
SLP-White: Lecithin, manufactured by Tsuji Oil Mills Co., Ltd., SLP-White, HLB = about 6

It was clarified from Table 11 that all of the emulsifying agents reduced off-flavor, and effectively suppressed the off-flavor over a long time period. Among them, it could be seen that even more remarkable effects were obtained in a case where a glycerol fatty acid ester is used.

Test Example 2-8

Effects of basic amino acids on deodorization and off-flavor suppression of refined fish oils were confirmed.

Specifically, to 75 g of a refined fish oil (manufactured by POLARIS, DHA content: 56% by weight, EPA content: 6% by weight) were added emulsifying agents 7 g of diglycerol monocaprate (manufactured by Taiyo Kagaku Co., Ltd, SUNSOFT Q-10D, HLB=9.5), 10 g of diglycerol monolaurate (manufactured by Taiyo Kagaku Co., Ltd, SUNSOFT Q-12D, HLB=8.5), 2 g of hexaglycerol condensed ricinoleate (manufactured by Taiyo Kagaku Co., Ltd, SUNSOFT No. 818H, HLB=about 2), and 1 g of hexaglycerol octastearate (manufactured by Taiyo Kagaku Co., Ltd, SUNFAT PS-68, HLB=3.5), the mixture was sufficiently stirred at 40° C. with a paddle blade agitator under nitrogen atmosphere, and 5 g of an amino acid: powder arginine was then gradually added thereto while stirring. Thereafter, the mixture was stirred well for 10 minutes, to give a DHA, EPA-containing refined fish oil formulation (Example 2-33). Also, as to the formulations to which an emulsifying agent and the amino acid were not added, the volume reduced by the absence of blending was not compensated, so that a total volume would be 75 g (Comparative 2-51). Here, a weight ratio of the polyunsaturated fatty acid to the amino acid and/or peptide [polyunsaturated fatty acid/(basic amino acid+basic peptide)] was 9.3/1, and a weight ratio of the polyunsaturated fatty acid to the emulsifying agent [polyunsaturated fatty acid/emulsifying agent] was 2.3/1.

The formulations obtained were divided in three aliquots and tightly sealed, which were evaluated as follows.
Sample for evaluating initial fish odor: sample that was allowed to stand at 25° C. for 10 minutes,
Sample A for evaluating off-flavor: sample that was allowed to stand at 55° C. for 24 hours, and
Sample B for evaluating off-flavor: sample that was allowed to stand at 37° C. for 2 months.

The fish-like odor of each of the samples after storage was subjected to sensory evaluation. Specifically, the seal of the samples obtained was opened, and the odor was directly confirmed, and the level of senses felt by the panelists was scored, and a score average of 10 panelists was calculated by defining a case where no fish odor was found as 0, and a case where a fish odor was strongly felt as 10. As to normalization of the score, the normalization was carried out so that a score average of the initial fish odor of Reference Example 2-51 would be 5, and comparisons were made between the samples. The results are shown in Table 12.

TABLE 12

|  | Comp. Ex. 2-51 | Ex. 2-33 |
|---|---|---|
| Refined Fish Oil | ○ | ○ |
| Emulsifying Agents | — | ○ |
| Arginine | — | ○ |
| Initial Fish Odor | 5.0 | 2.6 |
| Off-Flavor A (55° C., 24 h) | 9.1 | 2.8 |
| Off-Flavor B (37° C., 2 M) | 9.8 | 2.9 |

It was clarified from Table 12 that the basic amino acid more remarkably suppresses off-flavor. On the other hand, in Comparative Example 2-51 without adding an emulsifying agent and an amino acid, it could be seen that the effects on reducing off-flavor could not be found.

Formulation Examples will be given hereinbelow.

Formulation Example

Cookies

Twenty-six grams of salted butter is melted at an ambient temperature, and mixed well, and 14 g of white sugar is added thereto, and the mixture is mixed well until no rough spots are found. Thereto are supplied 55 g of cake flour and 5 g of an emulsion formulation prepared in Example 2-6, and the mixture is sufficiently mixed. The dough obtained is shaped and wrapped with clear-plastic wrap, and allowed to stand at 4° C. for one hour, and thereafter the shaped dough was cut and formed. The shaped product was baked at 160° C. for 25 minutes, to give 420 mg DHA, EPA-blended cookies.

Formulation Example

Bread

To 250 g of strong flour, 7 g of a dry yeast, 15 g of white sugar, and 3 g of table salt is supplied a mixture prepared by mixing 146 g of warm water at about 30° C. with 14 g of an emulsion formulation prepared in Example 2-7, and the mixture is kneaded until it is smoothly shaped. Thereto is mixed well 5 g of butter previously melted at an ambient temperature. The dough obtained is shaped and placed in a bowl to which oil is previously applied, and subjected to primary fermentation at 30° C. for one hour or so. The dough is divided in two parts, and each is shaped again, and allowed to rest for about 5 minutes. Thereafter, the dough is degassed, folded in three and shaped, and placed in a mold to which oil is previously applied. The lid is placed, and the dough is subjected to secondary fermentation at 30° C. for one hour or so. The mold with a lid is placed in an oven previously heated to 190° C., and baked for 30 minutes, and further baked after removal of the lid for 5 minutes, The baked product is quickly removed from the mold, and cooled on a net, to give DHA, EPA 1176 mg-blended bread.

Formulation Example

Fruits Preparation

Thirty-five grams of granulated sugar is added to 50 g of strawberries, and allowed to stand overnight in a refrigerator. The sugared strawberries are cooked at 90° C. for 5 minutes, while stirring well. Thereto is supplied a mixed solution prepared by adding to 8.6 g of water, 0.3 g of pectin, 0.5 g of sodium citrate, and 5 g of an emulsion formulation prepared in Example 2-8, and the mixture is heated to 80° C. or so to sufficiently dissolve. After stirring well, 0.2 g of citric acid and 0.4 g of fresh lemon juice are added thereto, the mixture is heated to 90° C. and then cooled, to give DHA, EPA 420 mg-blended fruits preparation.

Formulation Example

Salad Dressing

Eighteen grams of salt, 40 g of rice vinegar, and 10 g of wine vinegar are stirred until no insolubles are left. Thereto are added 50 g of salad oil, 25 g of olive oil, and 8 g of a fat or oil formulation prepared in Example 2-2, and the mixture is sufficiently stirred, to give a DHA, EPA 2041 mg-blended salad dressing.

Formulation Example

Ice Cream

Eighty grams of powdered skim milk, 120 g of granulated sugar, 2 g of glycerol stearate, 0.6 g of guar gum, 0.6 g of locust bean gum, 0.2 g of carrageenan, and 100 g of an emulsion formulation prepared in Example 2-9 are dissolved in 614.6 g of water heated to 60° C. Thereto is supplied 80 g of coconut oil, the mixture is sufficiently mixed, and then homogenized with a homogenizer at a pressure of 150 kgf/cm$^2$. This homogenized mixture is sterilized at 85° C. for 15 seconds, and rapidly cooled to 5° C. or lower, 2 g of vanilla flavor is then added thereto, and sufficiently mixed, and the mixture is then aged overnight at 5° C. This aged mixture is frozen in a continuous ice cream freezer with a 30% overrun, and filled into a cup from an outlet temperature-controlled to −5° C., and rapidly frozen at −40° C., to give DHA, EPA 8,400 mg-blended ice cream.

Formulation Example

Custard Pudding

Eighteen grams of raw whole egg, 10 g of granulated sugar, 64 g of cow milk, and 8 g of an emulsion formulation prepared in Example 2-10 are well mixed, and the mixture is filled into a cup. This filled cup is heated with a steamer at 90° C. for 20 minutes, and then cooled, to give DHA, EPA 672 mg-blended custard pudding.

Formulation Example

Jelly

The amount 0.4 g of carrageenan, 0.1 g of sodium citrate, and 10 g of granulated sugar are well mixed, and the mixture is supplied to 64.35 g of water while stirring. This liquid mixture is heated to 85° C. to sufficiently dissolve, and 5 g of an emulsion formulation prepared in Example 2-25 and 20 g of 100% orange juice are then added thereto, and the mixture is well mixed. Thereto is supplied 0.15 g of an orange flavor formulation, and the mixture is well mixed, filled in a cup, and cooled to be gelated, to give conjugated linoleic acid 1200 mg-blended jelly.

Formulation Example

Egg Granules

Five grams of a fat or oil formulation prepared in Example 2-27 is mixed with 10 g of whole egg powder, 15 g of cornstarch, 25 g of flour, and 30 g of white sugar, and 30 g of water is then supplied thereto, and the liquid mixture is kneaded well together. This kneaded mixture is supplied to an extrusion molding machine, and the molded product obtained is air-dried with a tray dryer. The dried product obtained is pulverized, to give DHA 1,134 mg-blended egg granules.

Formulation Example

Dried Seasoning Powder(Furikake)

Five grams of salted tea granules, 10 g of bonito granulated seasonings, 5 g of kombu granulated seasonings, 5 g of egg granules, 1 g of crumpled laver, 1 g of sesame, 1 g of dried sakura shrimp, and 1 g of a powder formulation prepared in Example 2-18 are mixed, to give a DHA, EPA 76 mg-blended Furikake.

Formulation Example

Instant Soup

To 500 g of water are added 10 g of flaky chicken broth, 5 g of soy sauce, 4 g of sesame oil, and 16 g of an emulsion formulation prepared in Example 2-23, and boiled. Thereto 100 g of beaten eggs are introduced while swirling, and heating is stopped. The soup obtained is cooled, and then subjected to lyophilization, to give conjugated linoleic acid 3,840 mg-blended instant soup.

Formulation Example

Retort Pouched Curry

The amount 4.5 g of coconut oil, 4.5 g of rapeseed oil, and 7.5 g of wheat flour are mixed while heating at 140° C., and 4.2 g of curry powder and 1.5 g of table salt are then added thereto and well mixed. Thereto are added 5.4 g of sugar, 1.8 g of sodium glutamate, 12 g of minced onions, 2.4 g of granulated beef extract, 1 g of Worcester's sauce, 1 g of soy sauce, 2.5 g of a fat or oil formulation prepared in Example 2-1, and 120 g of water, and the mixture is mixed while heating at 90° C. for 15 minutes. Thereto are added 8 g of beef, 8 g of potatoes, and 6 g of carrot, and the mixture is placed in a retort pouch and filled and sealed. This pouch is subjected to retort processing at 121° C. for 30 minutes, to obtain DHA, EPA 638 mg-blended retort pouched curry.

Formulation Example

Milk Beverage

To 6 or 60 g of an emulsion formulation prepared in Example 2-7 is mixed cow milk so as to make up a total amount of 1,000 g, and the mixture is homogenized with a homogenizer at a pressure of 150 kgf/cm$^2$, to obtain DHA, EPA 504 mg- or 5,040 mg-blended milk beverage. In addition, this milk beverage is subjected to spray drying, to give DHA, EPA 5040 mg-blended powdered milk.

Formulation Example

Fermented Milk Beverage

Water is mixed to 500 g of yogurt, 100 g of fructose-glucose liquid sugar, 2 g of pectin, and 0.4 g, 4 g, or 40 g of an emulsion formulation prepared in Example 2-6 so as to make up a total amount of 1,000 g, and the mixture is homogenized with a homogenizer at a pressure of 150 kgf/cm$^2$, to give DHA, EPA 33.6 mg-, 336 mg-, or 3,360 mg-blended fermented milk beverage.

Formulation Example

Coffee Beverage

Boiling water in an amount of about 10 times the weight is added to 200 g of coffee beans (L value: 27), to give 2,000 g of a coffee extract of Bx.2.6. Using this extract, a coffee beverage is prepared in accordance with a proportion shown in the following <Formulation 1>. To 178.5 g of this coffee beverage is added 1.5 g of an emulsion formulation prepared in Example 2-22, and the mixture is then packed in a 180 ml can, and sterilized (at 121° C. for 30 minutes), to give conjugated linoleic acid 360 mg-blended coffee beverage.

TABLE 13

<Formulation 1>

| Raw Material Name | Formulation Proportion (%) |
|---|---|
| Coffee Extract | 50.00 |
| Granulated Sugar | 6.00 |
| Cow Milk | 13.00 |
| pH Adjusting Agent (Sodium Bicarbonate) | 0.13 |
| Sucrose Fatty Acid Ester (HLB: 16) | 0.03 |
| Water | 30.84 |
| Total | 100.00 |

Formulation Example

Tablet

Fifteen grams of a powder formulation prepared in Example 2-19, 35 g of powdered reduced maltose syrup, 46 g of starch degradation product (DE value: 16), 3 g of sucrose behenate, and 1 g of fine silicon oxide powder are mixed, and the mixture is tableted with a tableting machine with a tabletting pressure of 100 kgf/cm$^2$, to give DHA, EPA 1,141 mg-blended tablet.

Formulation Example

Soft Capsules

Fifty-five grams of a fat or oil formulation prepared in Example 2-1, 40 g of diglycerol laurate (manufactured by Taiyo Kagaku Co., Ltd., SUNSOFT Q-12D), and 5 g of polyoxyethylene sorbitan fatty acid ester are mixed until the mixture becomes homogenous, and the mixture is filled in a soft capsule with a filling machine, to give DHA, EPA 14,033 mg-blended soft capsule.

Formulation Example

Hard Capsules

One hundred grams of a fat or oil formulation prepared in Example 2-33 is directly filled in a hard capsule with a filling machine, to give DHA, EPA 46,500 mg-blended hard capsule.

Formulation Example

Cosmetics (O/W Cream)

The amount 69.8 g of water, 3.3 g of glycerol, 0.5 g of glycerol laurate (manufactured by Taiyo Kagaku Co., Ltd., SUNSOFT No. 750-C), 1.5 g of decaglycerol oleate (manufactured by Taiyo Kagaku Co., Ltd., SUNSOFT Q-17Y-C), 0.1 g of decaglycerol diisostearate, and 0.4 g of xanthan gum are mixed, and heated at 70° C. to dissolve.

Next, 9.0 g of palm kernel oil, 3.0 g of MCT (glycerol caprylate/caprate triester (manufactured by Taiyo Kagaku Co., Ltd., SUNOIL MCT-7), 5 g of a fish oil (DHA content: 24% by weight, EPA content: 4% by weight) containing 1% by weight of arginine and 2% by weight of decaglycerol trioleate (manufactured by Taiyo Kagaku Co., Ltd., SUNSOFT Q-173Y) (DHA content: 24% by weight, EPA content: 4% by weight), 4.0 g of glycerol behenate-hexaglycerol octastearate blend (manufactured by Taiyo Kagaku Co., Ltd., TAISET 50-C), 0.4 g of diglycerol caprate (manufactured by Taiyo Kagaku Co., Ltd., SUNSOFT Q-10D-C), and 3 g of stearic acid are mixed, and heated at 70° C. to dissolve.

These solutions are stirred well with a homogenizer while applying shearing force. Thereafter, the stirring is stopped, and the mixture is cooled to room temperature, to give DHA, EPA 1,358 mg-blended cosmetics.

INDUSTRIAL APPLICABILITY

The flavor improver for a polyunsaturated fatty acid-containing fat or oil and the polyunsaturated fatty acid-containing fat or oil composition of the present invention can suppress the generation of unpleasant taste and flavor from the polyunsaturated fatty acid over a long time period, so that they can be suitably used as raw materials for, for example, foodstuff, pharmaceutical com*positions, and cosmetics.

The invention claimed is:

1. A polyunsaturated fatty acid-containing fat or oil composition, comprising
   (a) a fat or oil comprising a polyunsaturated fatty acid having 18 or more carbon atoms and two or more double bonds,
   (b) a basic amino acid and/or a basic peptide, wherein the basic amino acid, when present, comprises one or more members selected from the group consisting of lysine, arginine, histidine, and salts thereof, and wherein the basic peptide, when present, comprises one or more members selected from the group consisting of polylysine, polyarginine, polyhistidine, histone and protamine, and
   (c) an emulsifying agent, wherein the emulsifying agent comprises one or more emulsifying agents having an HLB value of less than 10,
   wherein the composition is an oil-in-water emulsion,
   wherein the weight ratio of the polyunsaturated fatty acid to the basic amino acid and the basic peptide, which is the polyunsaturated fatty acid/a total amount of the basic amino acid and the basic peptide, is from 30/0.01 to 5/1, and wherein the weight ratio of the polyunsaturated fatty acid to the emulsifying agent having an HLB value of less than 10, which is the polyunsaturated fatty acid/the emulsifying agent having an HLB value of less than 10, is from 100/0.01 to 0.2/1.

2. The fat or oil composition according to claim 1, wherein the polyunsaturated fatty acid comprises one or more members selected from the group consisting of DHA, EPA, and linoleic acid.

3. The fat or oil composition according to claim 1, wherein the emulsifying agent comprises one or more members selected from the group consisting of glycerol fatty acid ester and a polyglycerol fatty acid ester.

4. The fat or oil composition according to claim 3, wherein the fatty acid constituting the glycerol fatty acid ester or the polyglycerol fatty acid ester comprises a saturated or unsaturated fatty acid having 10 or more carbon atoms.

5. The fat or oil composition according to claim 1, wherein the weight ratio of the polyunsaturated fatty acid to the basic amino acid and the basic peptide, which is the polyunsaturated fatty acid/a total amount of the basic amino acid and the basic peptide, is from 30/0.01 to 9/1.

6. The fat or oil composition according to claim 1, wherein the weight ratio of the polyunsaturated fatty acid to the emulsifying agent having an HLB value of less than 10, which is the polyunsaturated fatty acid/the emulsifying agent having an HLB value of less than 10, is from 100/1 to 0.2/1.

7. The fat or oil composition according to claim 1, wherein the emulsifying agent comprises one or more members selected from the group consisting of glycerol fatty acid esters, sucrose fatty acid esters, propylene glycol fatty acid esters, and phospholipids.

8. Foods or beverages comprising a fat or oil composition as defined in claim 1.

9. A pharmaceutical composition comprising a fat or oil composition as defined in claim 1.

10. Cosmetics comprising a fat or oil composition as defined in claim 1.

11. The fat or oil composition according to claim 1, wherein an off-flavor is suppressed compared to the composition not having a basic amino acid and a basic peptide, wherein the off-flavor is evaluated after the composition is allowed to stand at 55° C. for 24 hours.

12. The fat or oil composition according to claim 1, wherein an off-flavor is suppressed compared to the composition not having a basic amino acid and a basic peptide, wherein the off-flavor is evaluated after the composition is allowed to stand at 37° C. for 3 months.

13. The polyunsaturated fatty acid-containing fat or oil composition according to claim 2, wherein the composition comprises a basic amino acid.

14. The polyunsaturated fatty acid-containing fat or oil composition according to claim 2, wherein the composition comprises a basic peptide.

15. The polyunsaturated fatty acid-containing fat or oil composition according to claim 2, wherein the composition comprises a basic amino acid and a basic peptide.

16. The fat or oil composition according to claim 5, wherein the weight ratio of the polyunsaturated fatty acid to the basic amino acid, which is the polyunsaturated fatty acid/a total amount of the basic amino acid, is from 30/0.01 to 9/1.

17. The fat or oil composition according to claim 5, wherein the weight ratio of the polyunsaturated fatty acid to the basic peptide, which is the polyunsaturated fatty acid/a total amount of the basic peptide, is from 30/0.01 to 9/1.

* * * * *